United States Patent [19]
Lehrman et al.

[11] Patent Number: 5,513,646
[45] Date of Patent: May 7, 1996

[54] PERSONAL SECURITY MONITORING SYSTEM AND METHOD

[75] Inventors: Michael L. Lehrman, Washington, D.C.; Michael D. Halleck, Northglenn; Michael E. Halleck, Longmont, both of Colo.

[73] Assignee: I Am Fine, Inc., Bethesda, Md.

[21] Appl. No.: 239,752

[22] Filed: May 9, 1994

Related U.S. Application Data

[63] Continuation-in-part of Ser. No. 187,787, Jan. 26, 1994, abandoned, which is a continuation of Ser. No. 973,299, Nov. 9, 1992, abandoned, and a continuation-in-part of Ser. No. 51,975, Apr. 26, 1993, abandoned.

[51] Int. Cl.$^6$ ..................................................... A61B 5/08
[52] U.S. Cl. ........................... 128/716; 128/903; 128/671
[58] Field of Search ............................. 128/670–1, 716, 128/903

[56] References Cited

U.S. PATENT DOCUMENTS

| | | |
|---|---|---|
| 4,491,970 | 1/1985 | LaWhite et al. . |
| 4,706,689 | 11/1987 | Man . |
| 4,757,824 | 7/1988 | Chaumet .................................. 128/716 |
| 4,760,593 | 7/1988 | Shapiro et al. . |
| 4,784,162 | 11/1988 | Ricks et al. . |
| 4,909,260 | 3/1990 | Salem et al. . |
| 5,022,402 | 6/1991 | Schieberl et al. . |
| 5,086,391 | 2/1992 | Chambers . |
| 5,226,416 | 7/1993 | Bethune et al. ...................... 128/716 X |
| 5,400,012 | 3/1995 | Walton ................................. 128/671 X |

*Primary Examiner*—Angela D. Sykes
*Attorney, Agent, or Firm*—Harold A. Burdick

[57] ABSTRACT

Personal security monitoring apparatus system and method are disclosed, the apparatus including a breath detector and signal processor worn by the user. The signal processor distinguishes between the user's normal breathing patterns and a preselected other breathing pattern intentionally executed by the user when in distress, an alarm output being generated when the other breathing pattern is recognized. The alarm output is transmitted to a local receiver for retransmission over local telephone service to a remote monitoring station. The other breathing pattern may be selected by the user from a plurality of possible other patterns.

19 Claims, 26 Drawing Sheets

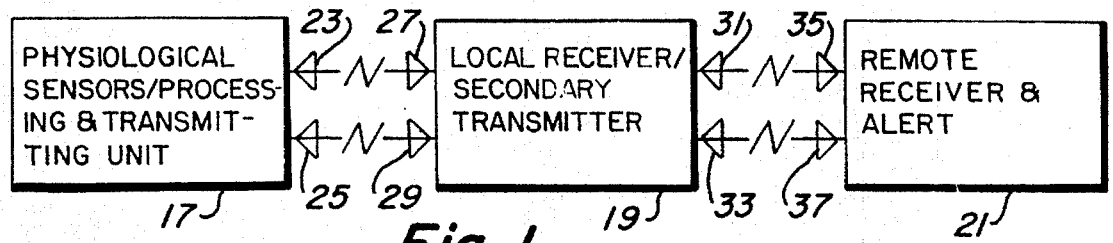
Fig_1
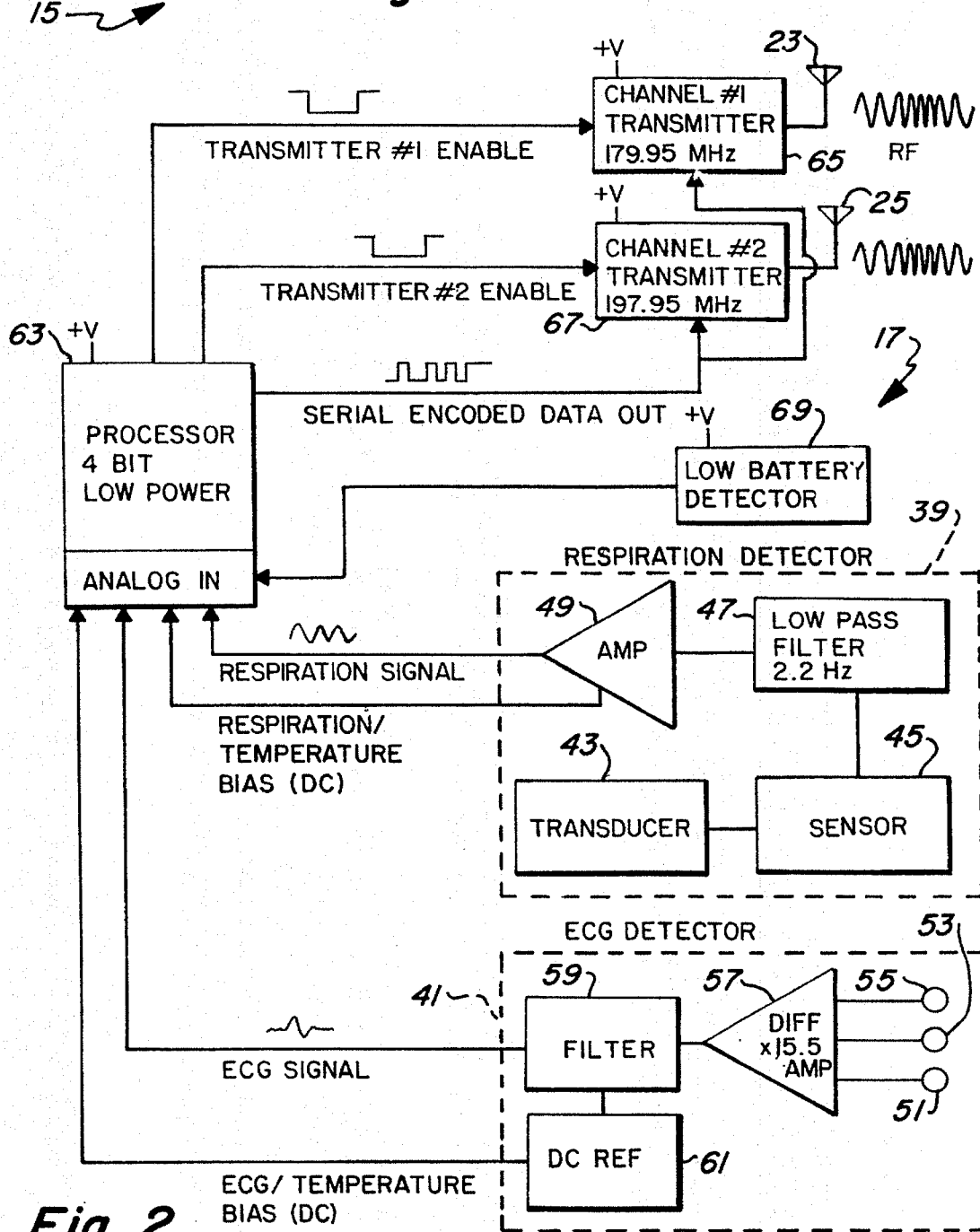
Fig_2

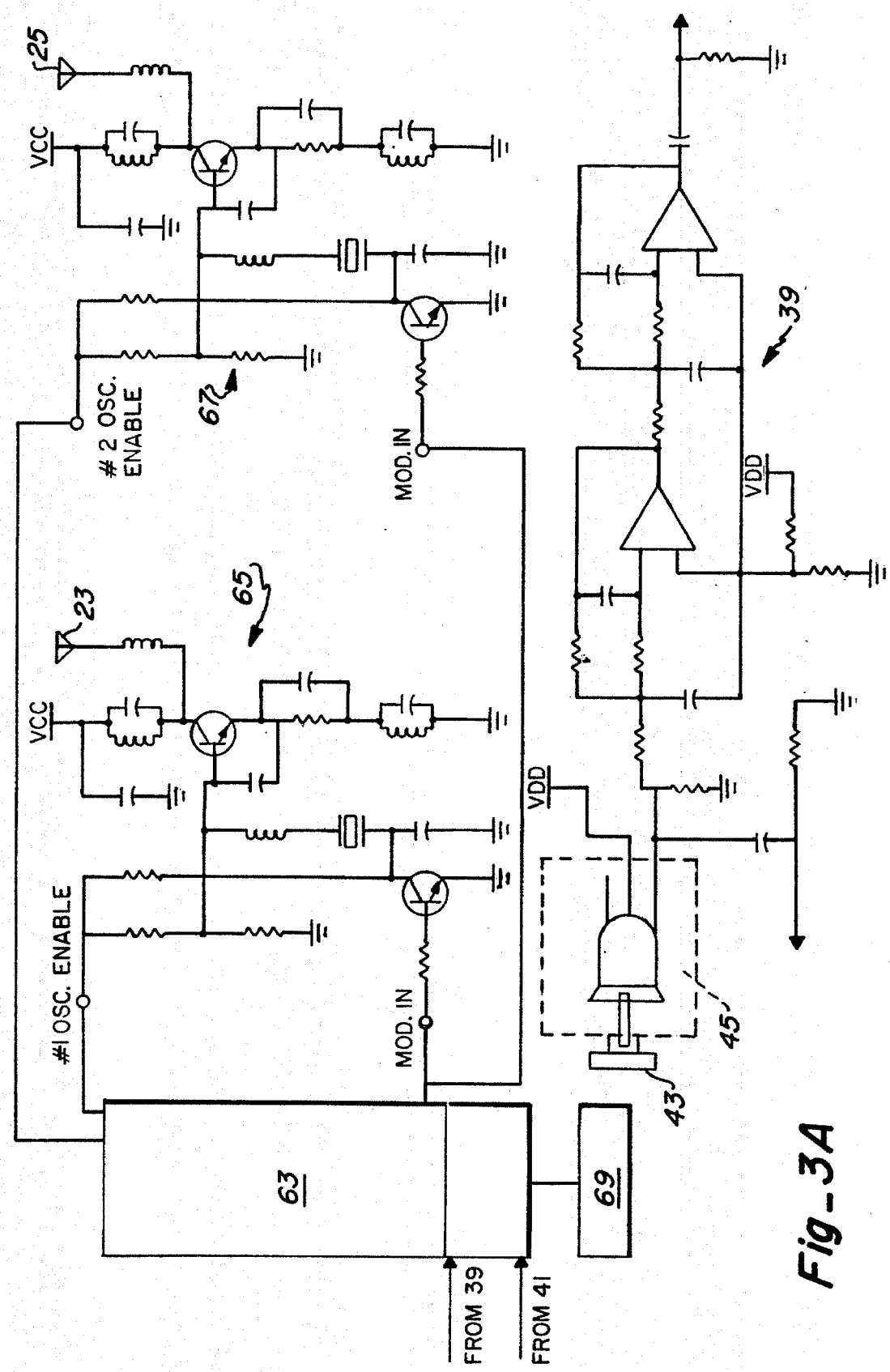
Fig_3A

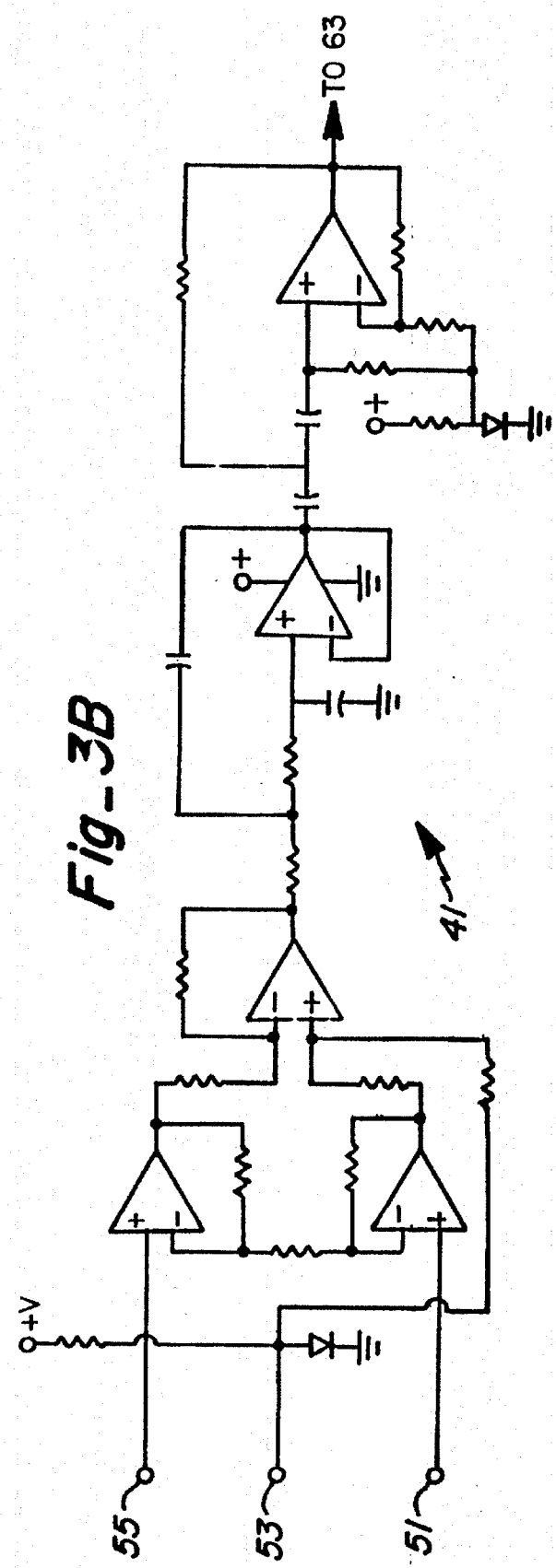
Fig_3B

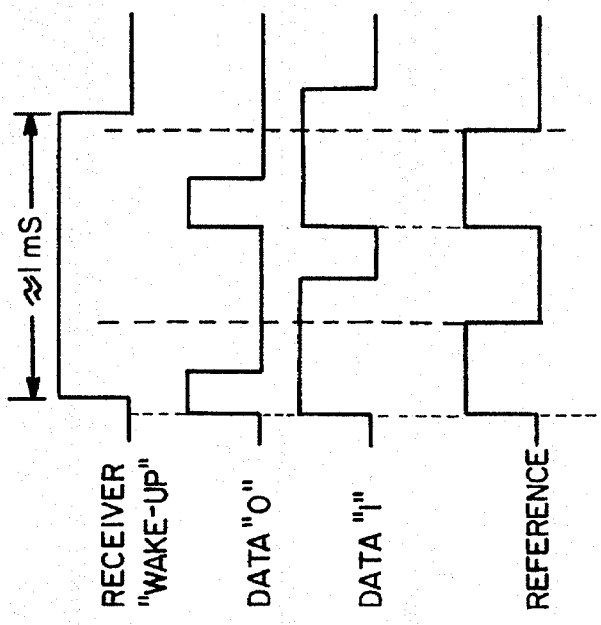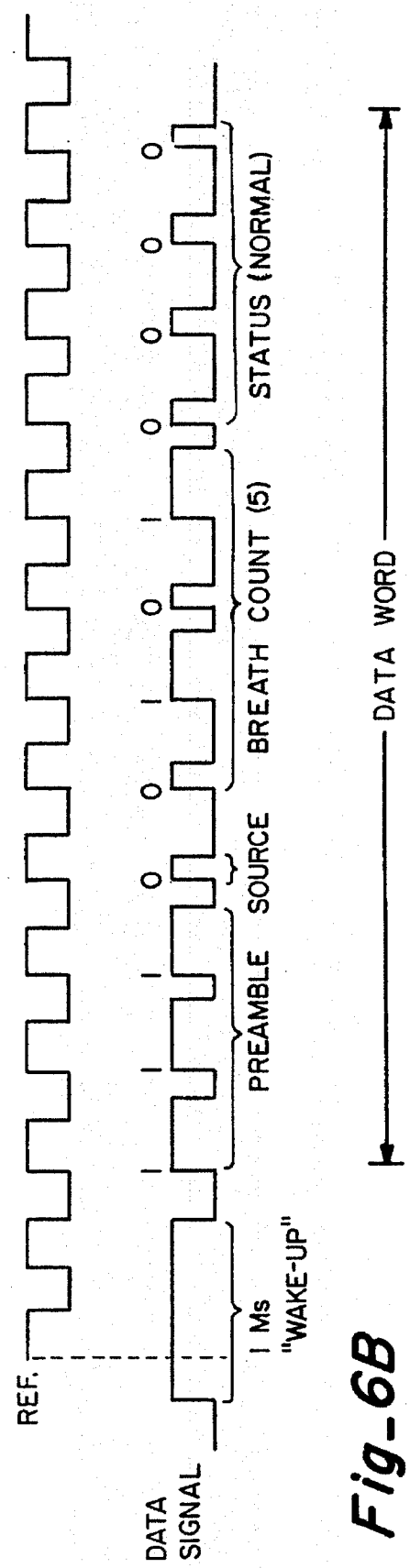

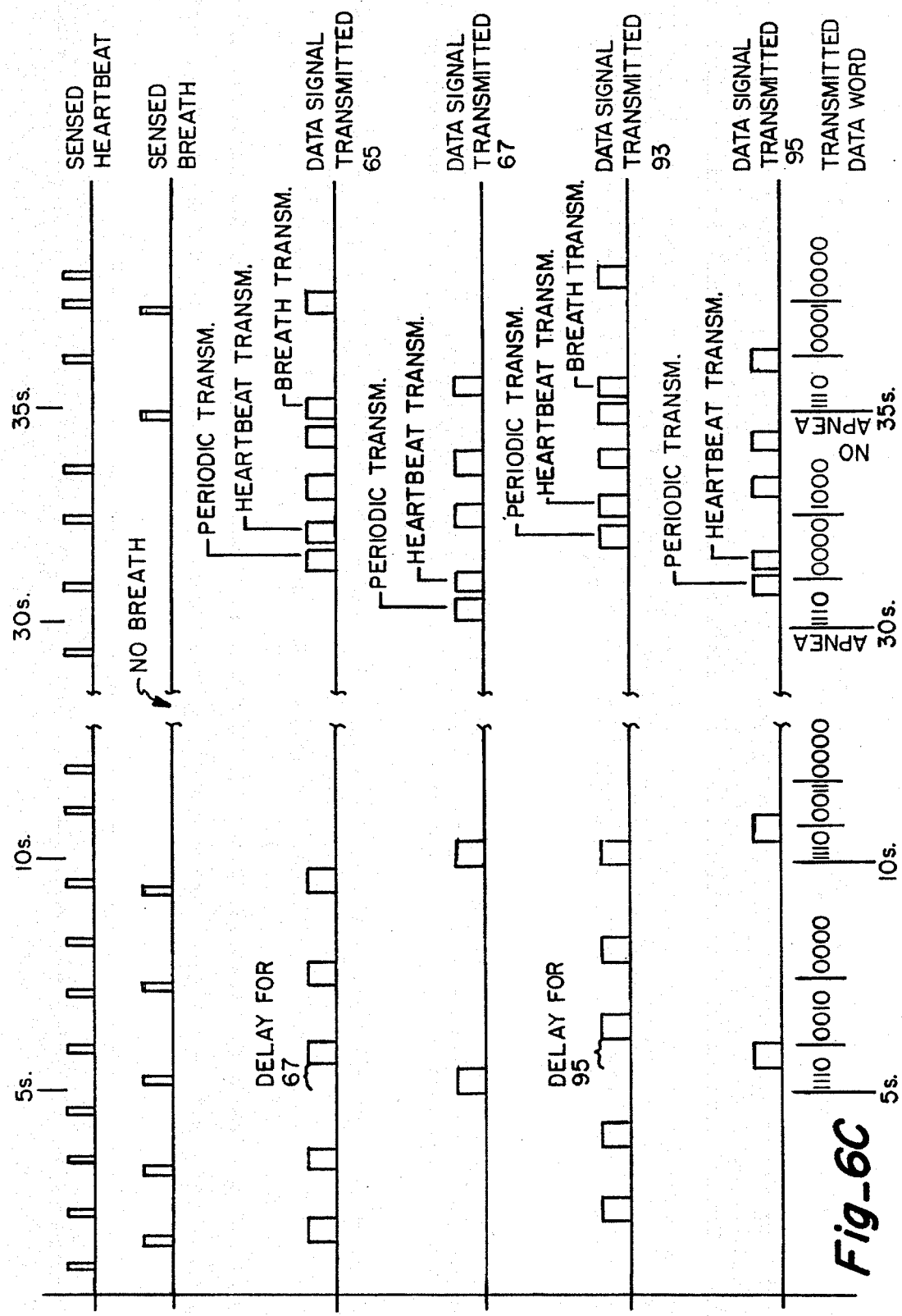
Fig_6C

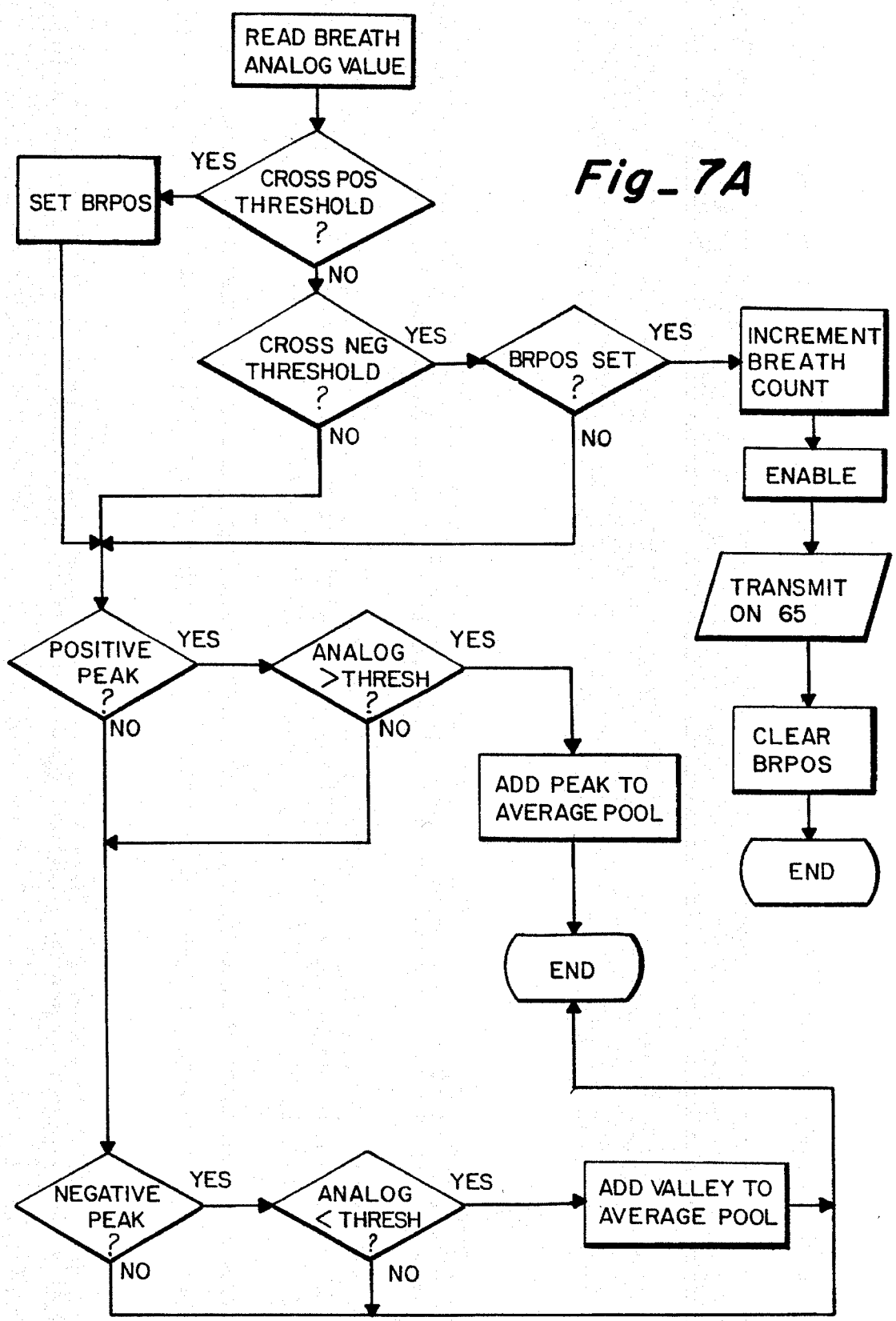
Fig_7A

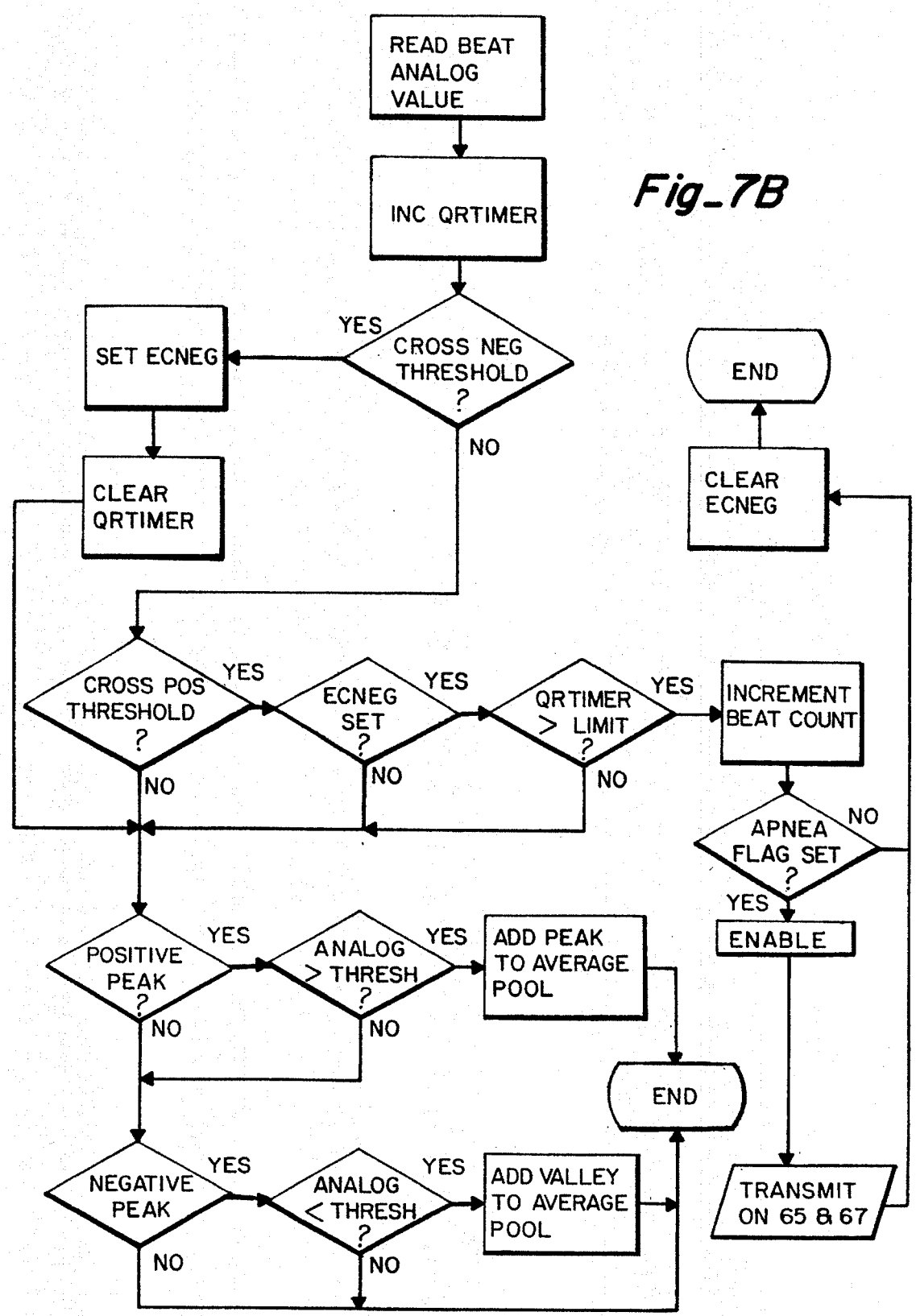
Fig_7B

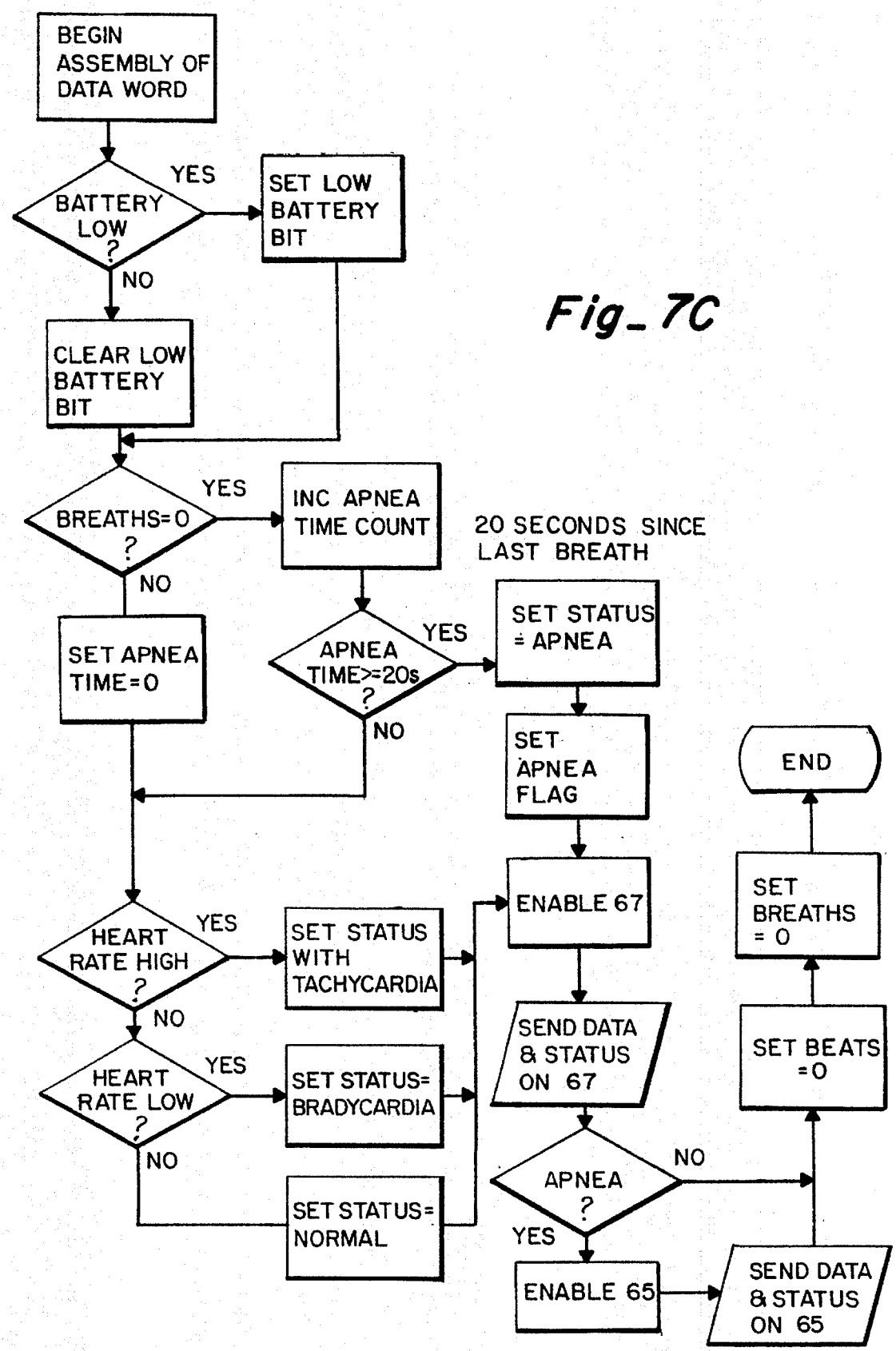
Fig_7C

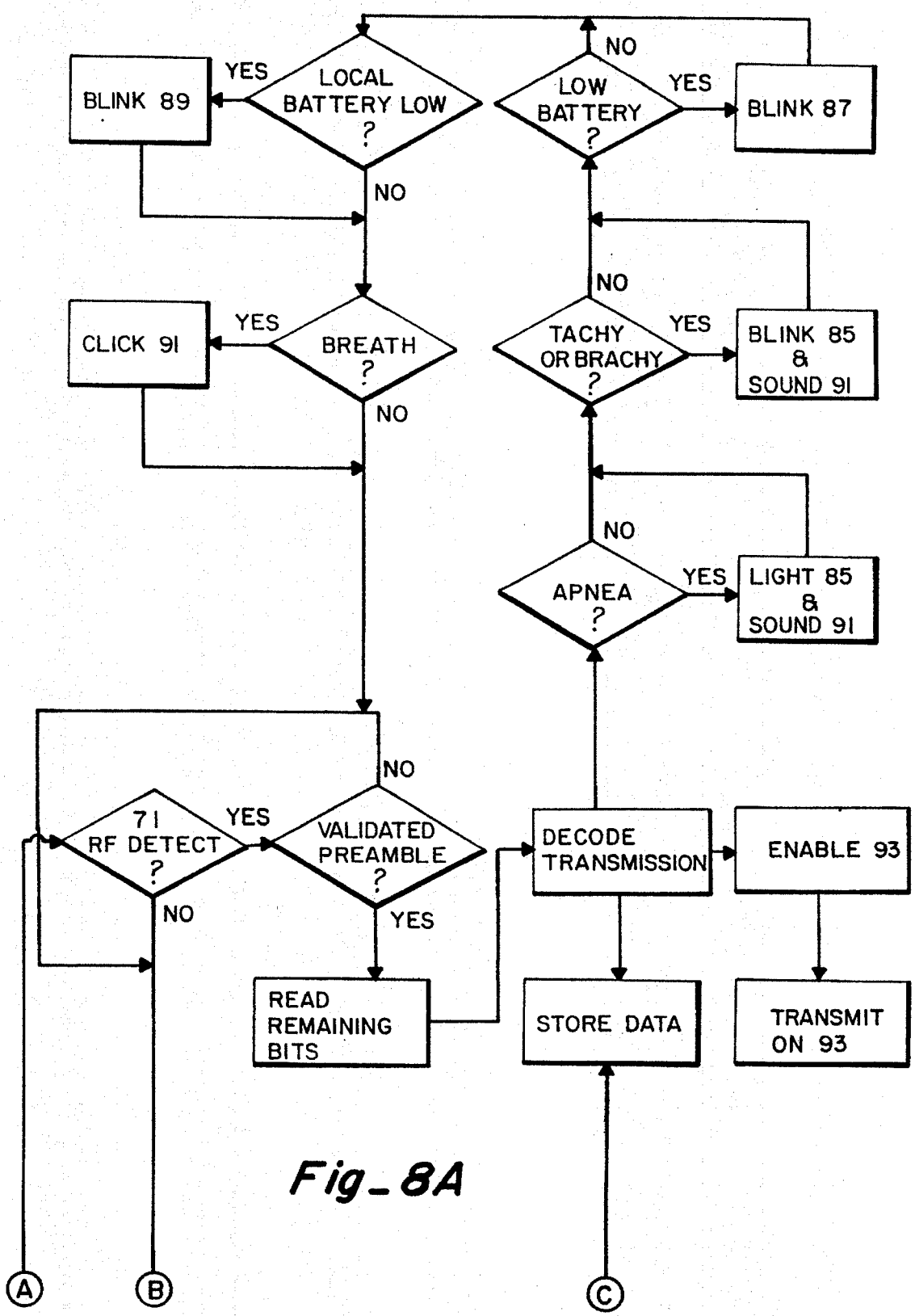
Fig_8A

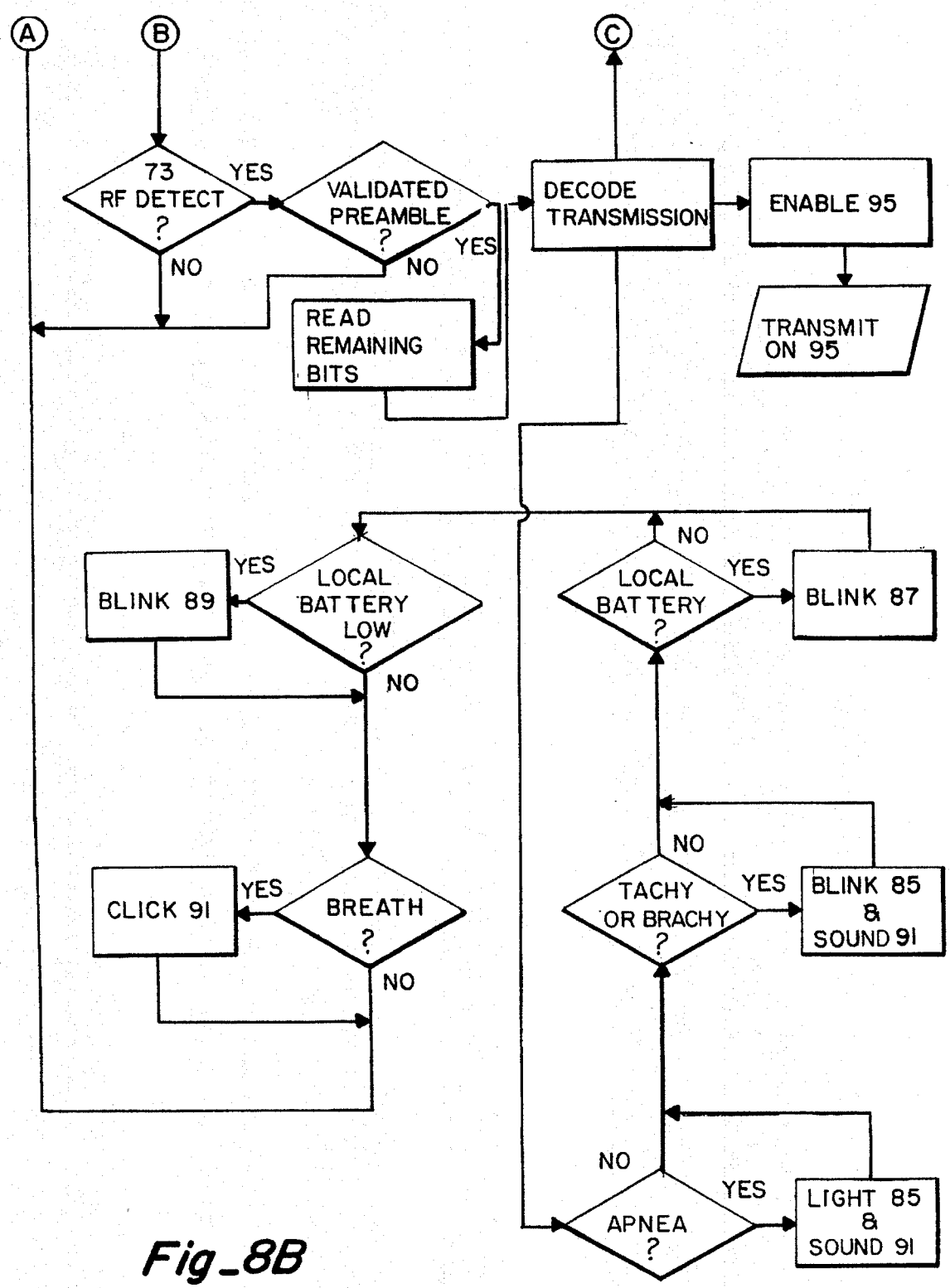
Fig_8B

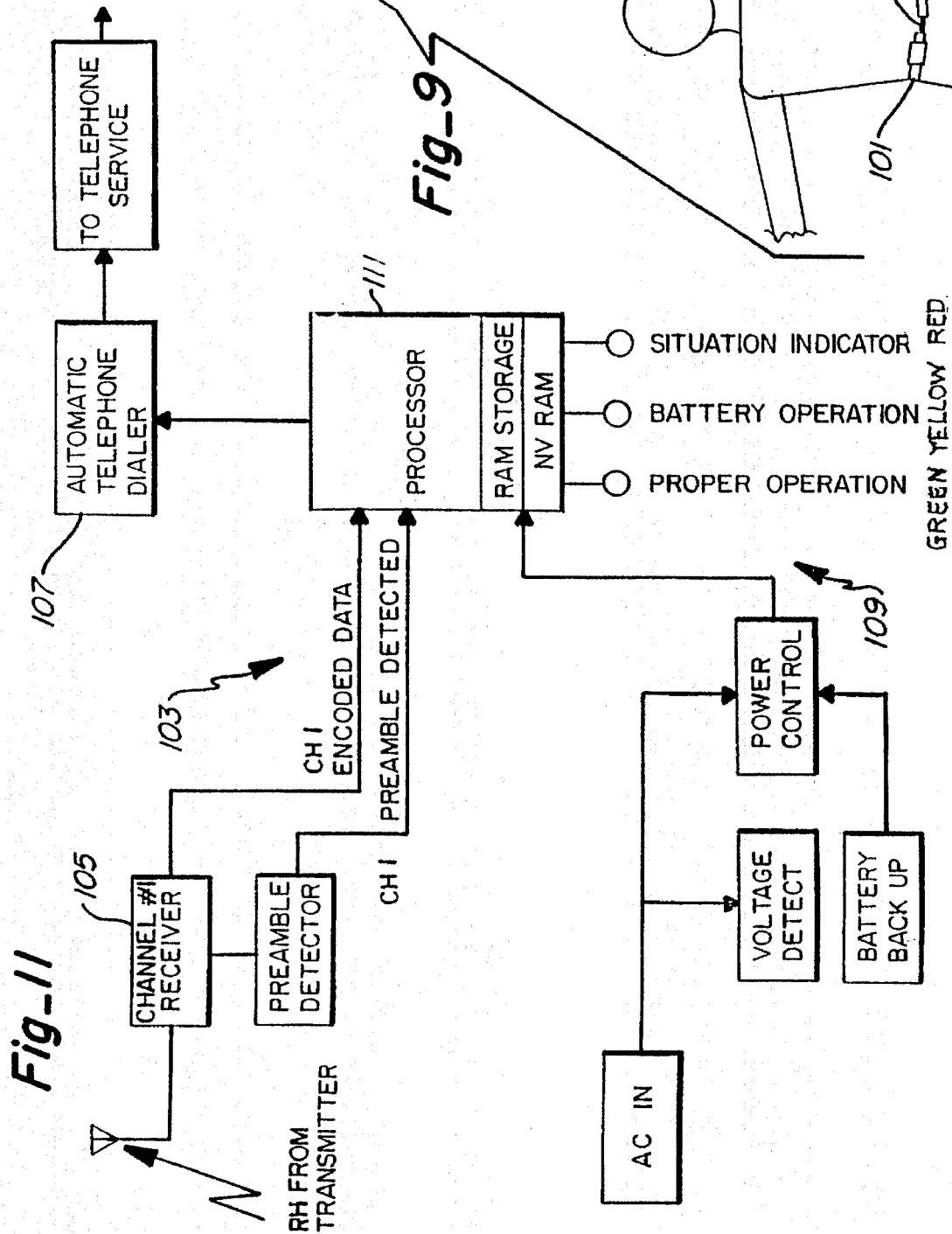

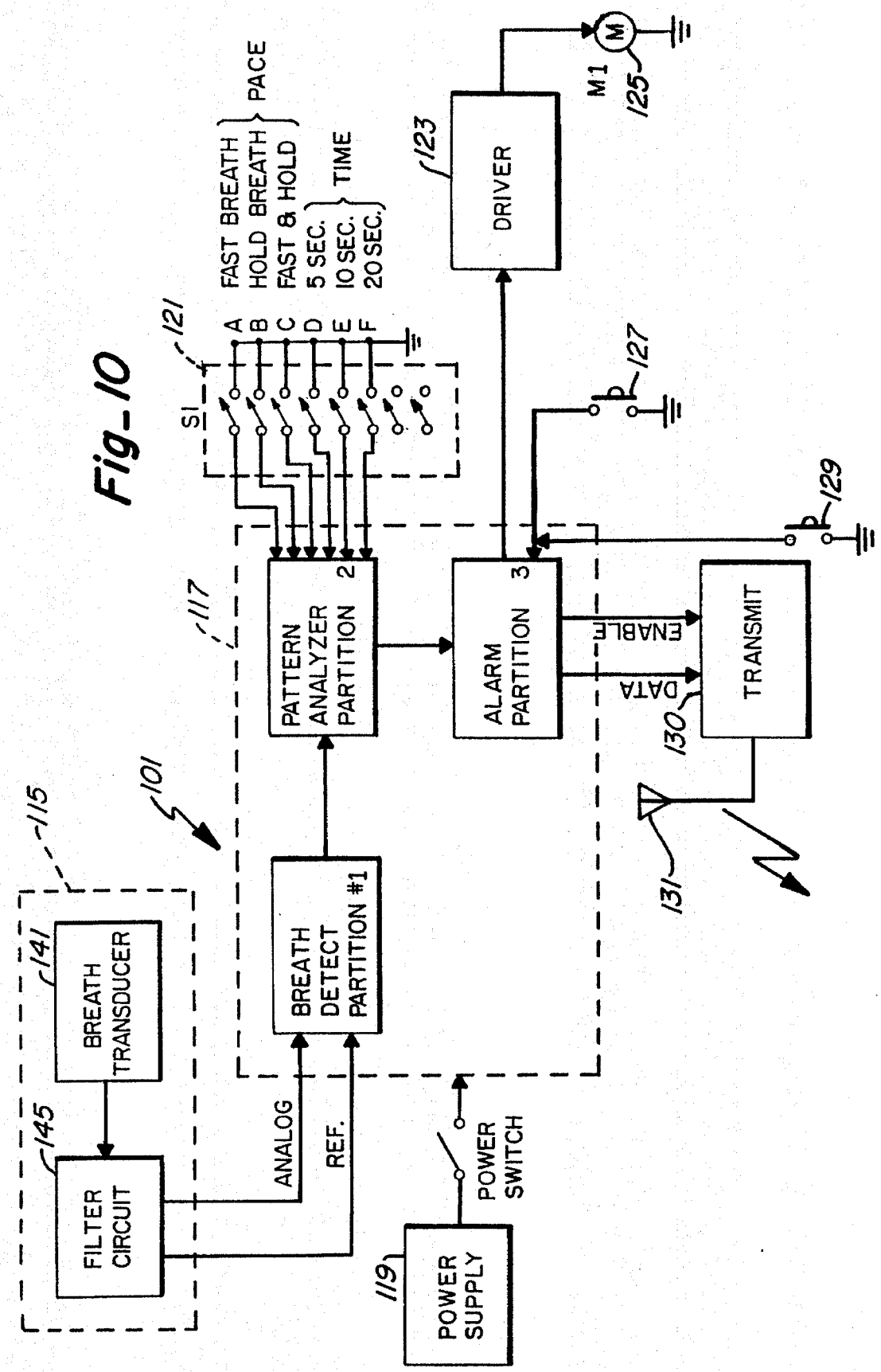
Fig_10

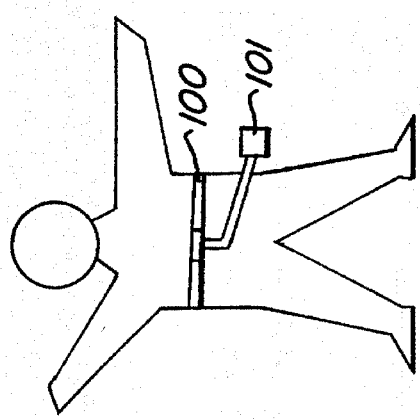
Fig_12A
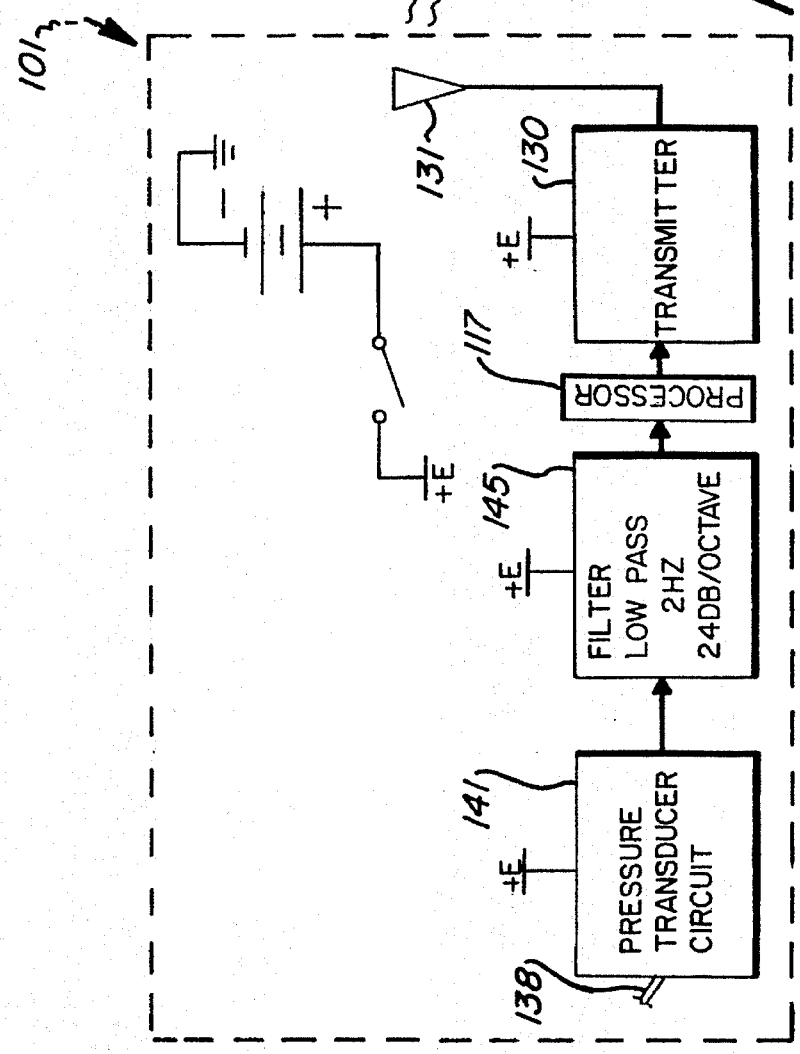
Fig_12B

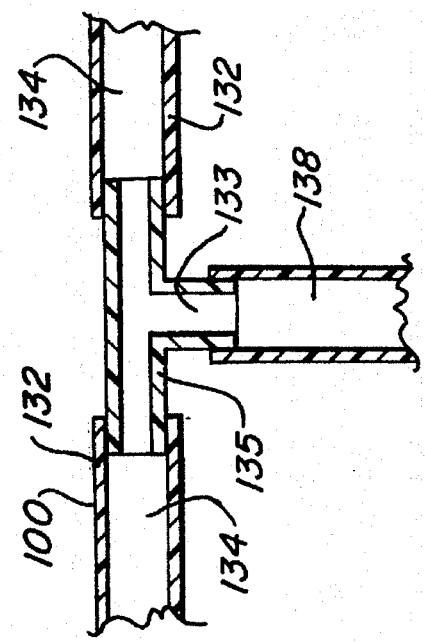
Fig_14
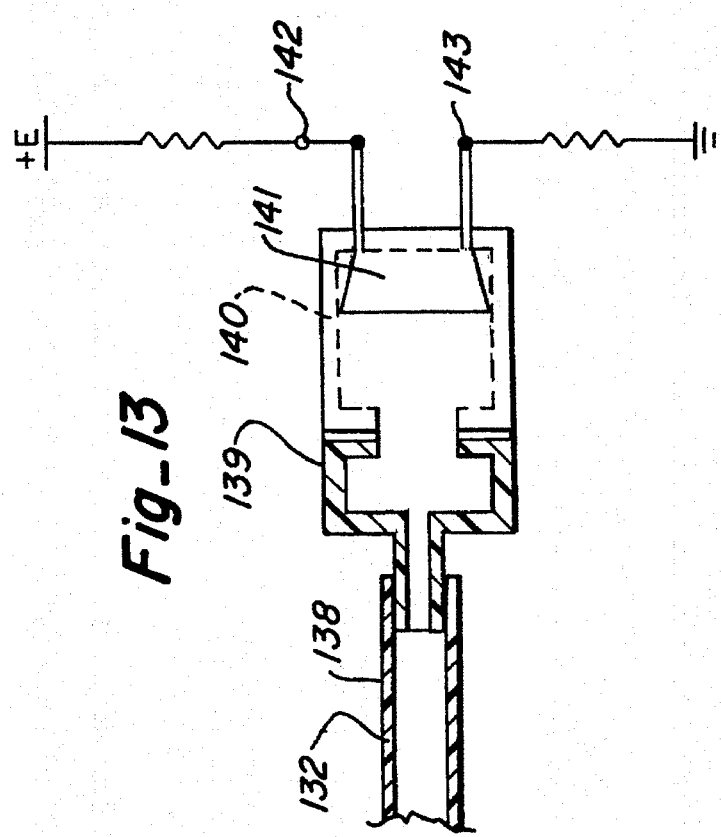
Fig_13

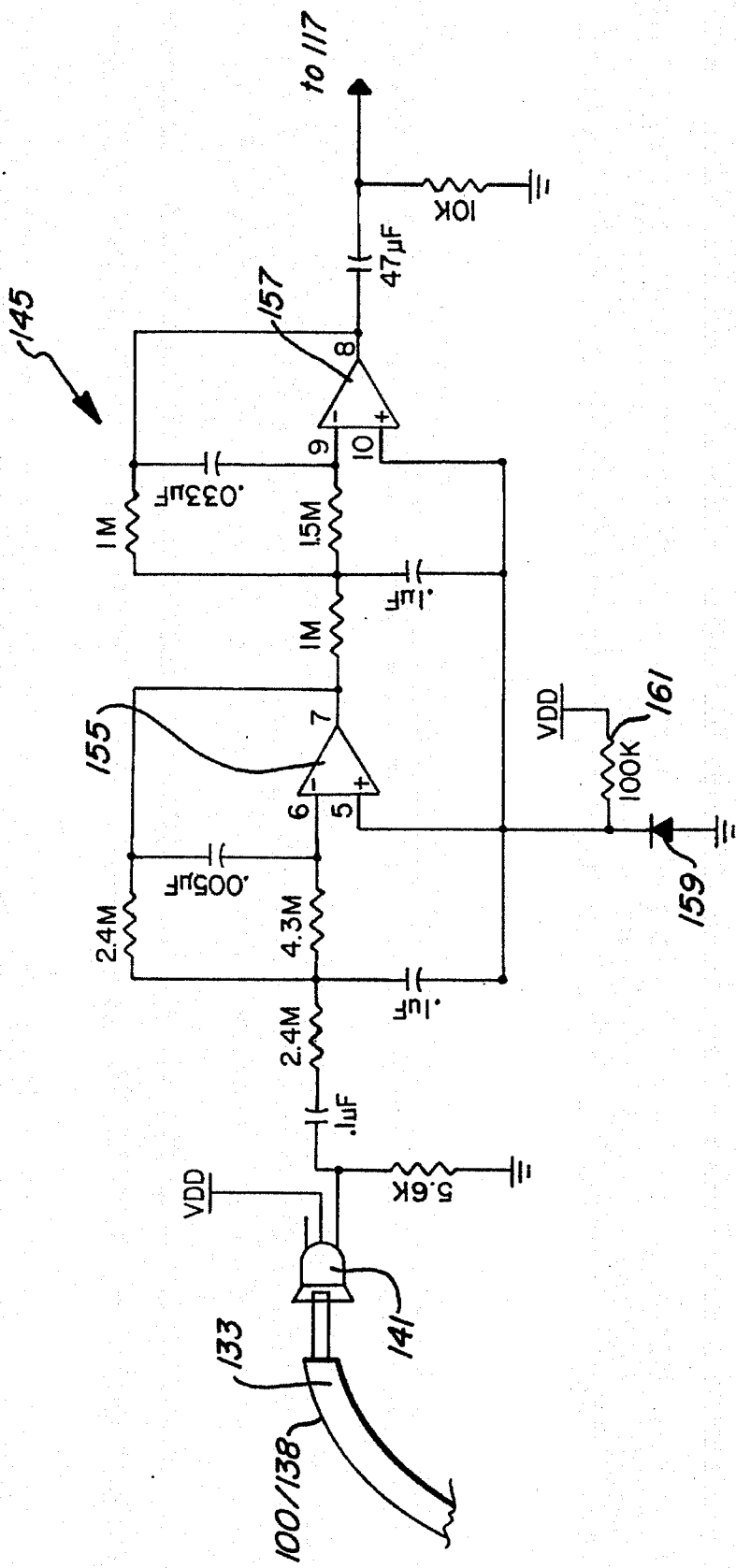
Fig_15

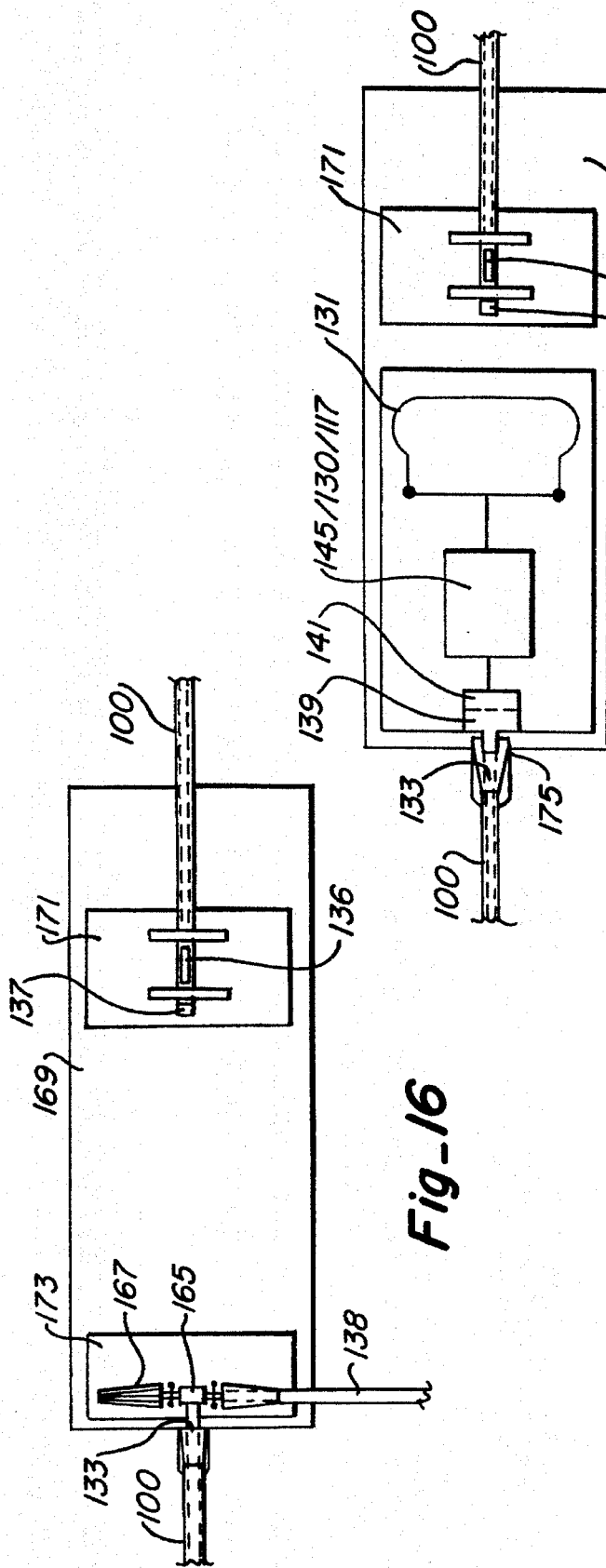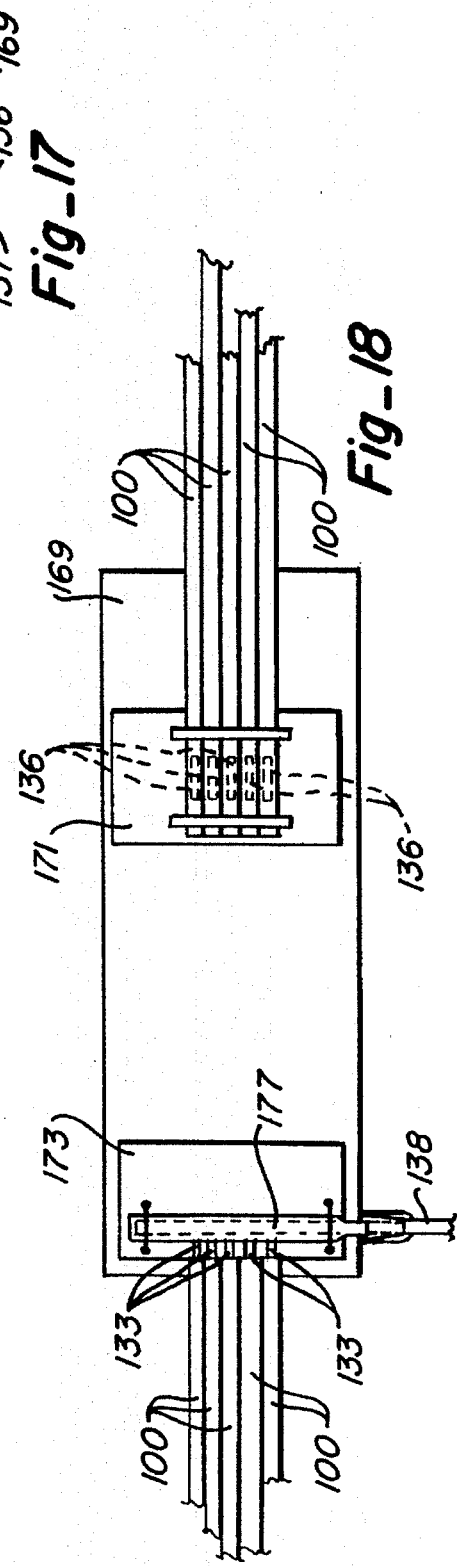

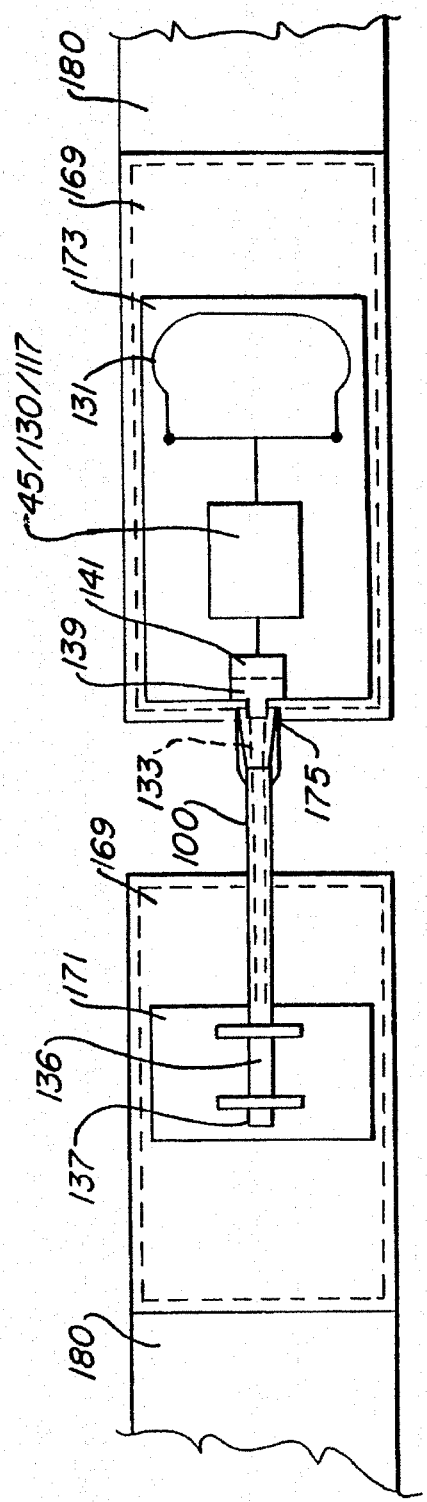
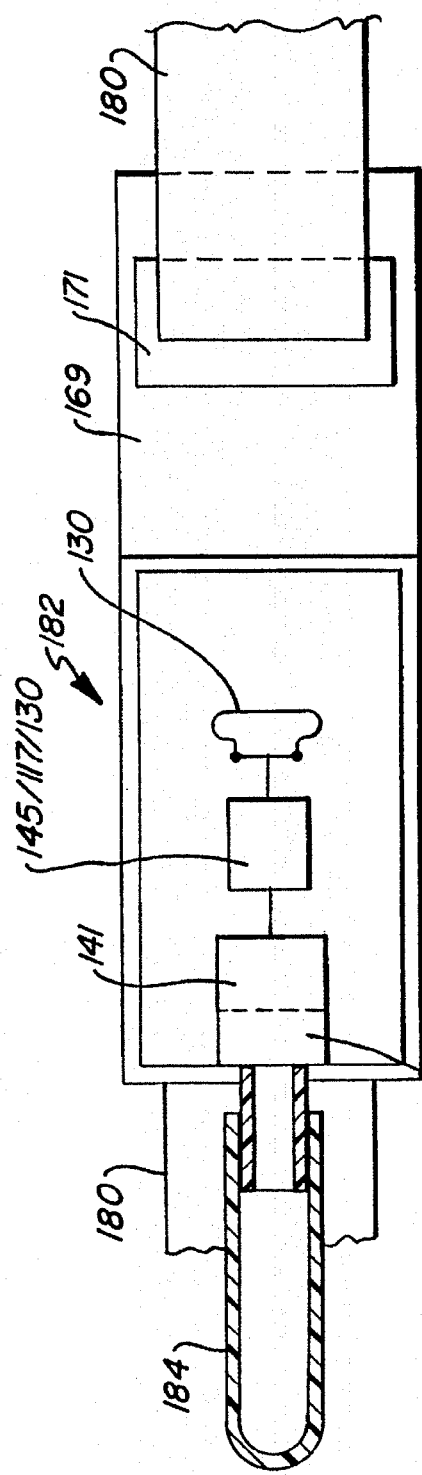
Fig.-21
Fig.-22

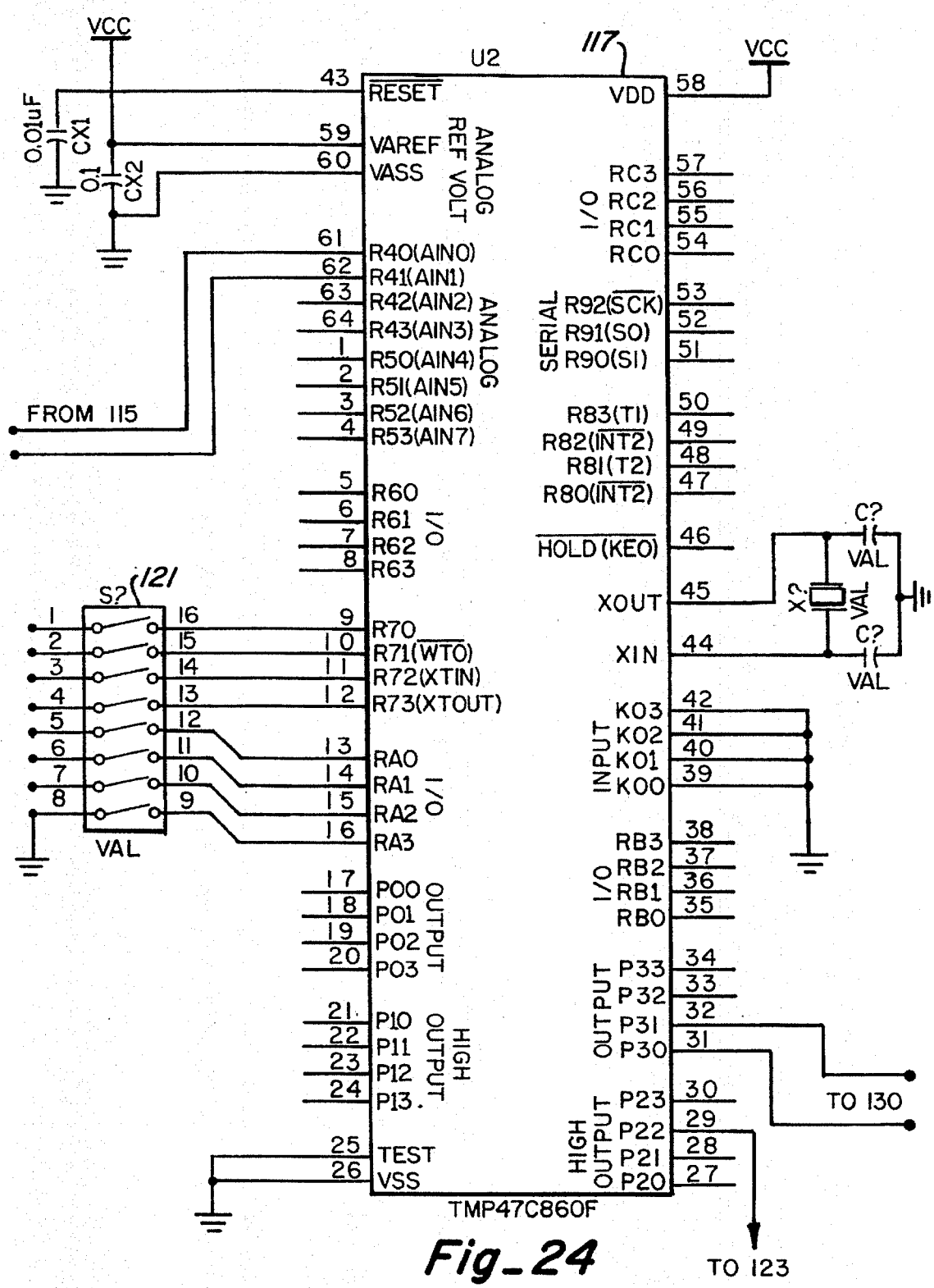
Fig_24

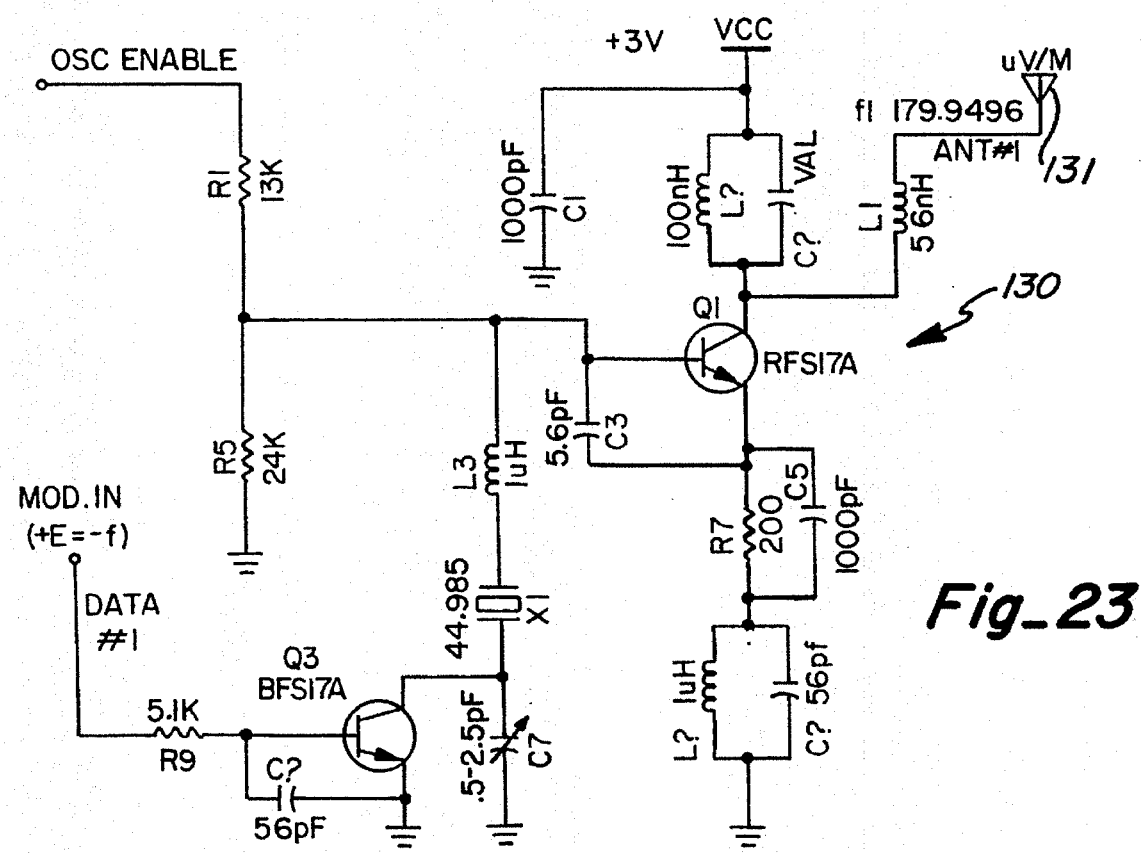
Fig_23
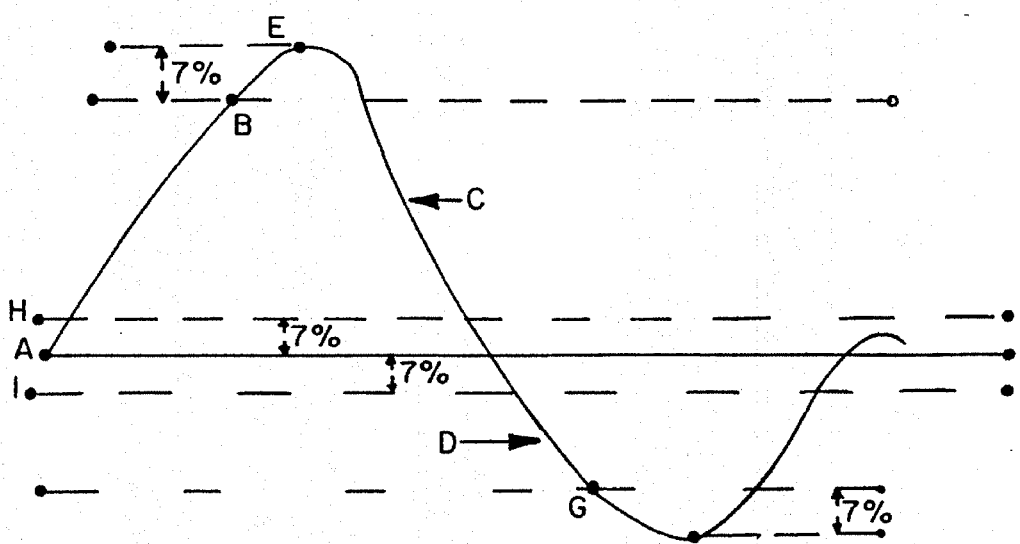
Fig_25

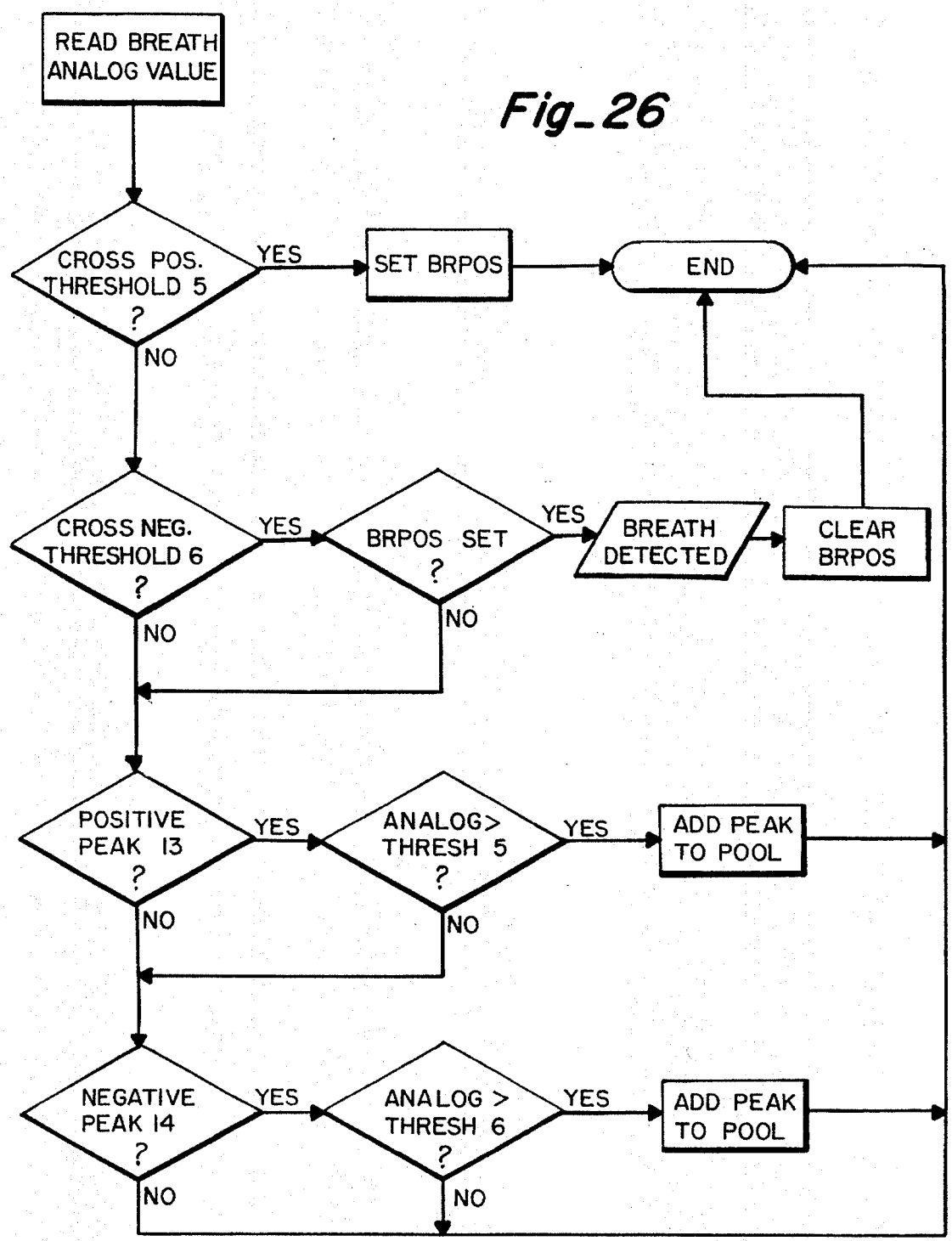
Fig_26

PERSONAL SECURITY MONITORING SYSTEM AND METHOD

RELATED APPLICATIONS

This application is a continuation-in-part of U.S. patent application Ser. No. 08/187,787 (itself a continuation of U.S. patent application Ser. No. 07/973,299 filed Nov. 9, 1992, now abandoned) filed Jan. 26, 1994 and entitled "Apparatus and Method For Remote Monitoring of Physiological Parameters", now abandoned, and a continuation-in-part of U.S. patent application Ser. No. 08/051,975 filed Apr. 26, 1993 and entitled "Respiration Monitor With Simplified Breath Detector", now abandoned.

FIELD OF THE INVENTION

This invention relates to personal security systems, and, more particularly, relates to personal security monitoring devices and methods.

BACKGROUND OF THE INVENTION

Various emergency response monitors or like systems have been heretofore suggested and/or utilized which include a portion which is worn or held by the user (see, for example, U.S. Pat. Nos. 4,491,970, 5,086,391, 4,706,689, 4,784,162, 5,022,402, 4,909,260 and 4,760,593). Such systems have typically been of the constant transmission type (i.e., providing constant subject monitoring) or of the manual actuation type.

However, such heretofore known systems have often utilized complex and bulky, and thus conspicuous, monitoring units, have often required extensive battery capacity and FCC approval where constant transmission is utilized, have not provided for interception of false alarms, and/or have not provided for actuation without actual medical emergency and/or manual activation of an alarm transmission. Significant readaptation and/or further improvement of such systems and monitors could thus still be utilized, and particularly for use thereof in personal security monitoring systems.

SUMMARY OF THE INVENTION

This invention provides a personal security monitoring apparatus, system and method which is based on recognition of a preselected breathing pattern. The apparatus utilized in the system includes a respiration monitor and transmitter discretely worn by the user who's security is being monitored, the system including a local receiver which includes an auto-dialer or the like for sending an alarm to a monitoring station when alerted by a transmission from the user's monitor. The monitor relays such transmission upon recognition of a selected breathing pattern, and thus is actuatable without manual contact by the user with the apparatus.

The monitor is compact and body mountable, and includes a breath detector providing an output indicative of a user's respiration, means for receiving the output from the breath detector and utilizing the received output to distinguish between the user's normal breathing pattern and a preselected other breathing pattern to be intentionally executed by the user when in distress, and an output connected with the means for receiving the output for providing an alarm signal only upon recognition of the other breathing pattern.

A selector is provided at the monitor for user selection of the selected other breathing pattern from a plurality of possible breathing patterns. The system further includes a receiver for receiving the alarm signal transmitted from the output and retransmitting the alarm signal to a monitoring station.

The method for monitoring personal security includes the steps of detecting respiration of a person to be monitored, utilizing the detected respiration to establish the person's normal breathing patterns, selecting another breathing pattern to be intentionally executed by the person when in distress, distinguishing between the established normal breathing patterns and the other breathing pattern when executed by the person, and providing an alarm signal upon recognition of the other breathing pattern.

It is therefor an object of this invention to provide an improved personal security monitoring apparatus, system and method.

It is another object of this invention to provide a personal security monitoring apparatus and method based on recognition of a preselected breathing pattern.

It is another object of this invention to provide a personal security monitoring apparatus and method which transmits an alarm signal without manual actuation during a security breach.

It is still another object of this invention to provide a personal security monitoring system including a body mounted apparatus for detecting the user's normal breathing patterns and distinguishing the normal patterns from another pattern preselected by the user from a plurality of other patterns, a local receiver for receiving an alarm output from the apparatus when the other pattern is recognized, and means for retransmitting the alarm output to a remote monitoring station.

It is yet another object of this invention to provide a securing monitor that is compact and body mountable, and including a breath detector providing an output indicative of a user's respiration, means for receiving the output from the breath detector and utilizing the received output to distinguish between the user's normal breathing pattern and a preselected other breathing pattern to be intentionally executed by the user when in distress, and an output device connected with the means for receiving the output for providing an alarm signal only upon recognition of the other breathing pattern.

It is still another object of this invention to provide a personal security monitoring system having a monitor associated with a user to be monitored and including a breath detector providing an output indicative of a user's respiration, a selector for user selection of a selected breathing pattern from a plurality of possible breathing patterns, and a processor receiving the output from the breath detector and the selection from the selector, the processor utilizing the received output to distinguish between the user's normal breathing pattern and the selected breathing pattern and providing an alarm output only upon recognition of the selected breathing pattern.

It is yet another object of this invention to provide a method for monitoring personal security including the steps of detecting respiration of a person to be monitored, utilizing the detected respiration to establish the person's normal breathing patterns, selecting another breathing pattern to be intentionally executed by the person when in distress, distinguishing between the established normal breathing patterns and the other breathing pattern when executed by the person, and providing an alarm signal upon recognition of the other breathing pattern.

With these and other objects in view, which will become apparent to one skilled in the art as the description proceeds, this invention resides in the novel construction, combination, arrangement of parts and method substantially as hereinafter described, and more particularly defined by the appended claims, it being understood that changes in the precise embodiment of the herein disclosed invention are meant to be included as come within the scope of the claims.

BRIEF DESCRIPTION OF THE DRAWINGS

The accompanying drawings illustrate a complete embodiment of the invention according to the best mode so far devised for the practical application of the principles thereof, and in which:

FIG. 1 is a block diagram of an apparatus of this invention;

FIG. 2 is a block diagram of the sensor/transmitter unit of the apparatus of FIG. 1;

FIGS. 3A and 3B are a schematic diagrams of the sensor/transmitter unit of FIG. 2;

FIGS. 6A through 6C are graphic representations of output date formation and exemplary transmissions of the apparatus of this invention;

FIGS. 7A through 7C are flow charts illustrating operation of the sensor/transmitter unit of FIG. 2;

FIGS. 8A and 8B are flow charts illustrating operation of the local receiver/secondary transmitter of FIG. 4;

FIG. 9 is a schematic illustration of the preferred embodiment of this invention for use as a personal security monitor;

FIG. 10 is a block diagram of the body mounted monitoring apparatus shown in FIG. 1;

FIG. 11 is a block diagram of the local receiver used with the security monitoring system of this invention;

FIGS. 12A and 12B are schematic illustrations of the respiration monitor, including the breath detector, utilized with the security monitoring system of this invention;

FIG. 13 is a schematic illustration of the transducer assembly of the monitor of FIG. 12;

FIG. 14 is a sectional view of one arrangement for interconnection of the detector and transducer of FIGS. 12 and 13;

FIG. 15 is a schematic illustration of the transducer and low pass filter of the monitor of this invention;

FIG. 16 is an illustration of one means for maintaining the detector of this invention on the body of a user;

FIG. 17 is an illustration of a preferred arrangement of the monitor of this invention which is worn by a user;

FIG. 18 is an illustration of a second embodiment of the breath detector of this invention;

FIG. 21 is an illustration of another preferred arrangement of the breath detector of this invention;

FIG. 22 is an illustration of yet another embodiment of the breath detector of this invention;

FIG. 23 is a schematic of the on-body transmitter used in the monitor of FIG. 9;

FIG. 24 is a schematic of the on-body processor used in the monitor of FIG. 9;

FIG. 25 is an illustration of a single breath waveform; and

FIGS. 26 through 30 are a flow charts illustrating programming of the processor of FIG. 24.

DESCRIPTION OF THE INVENTION

Figure 4:
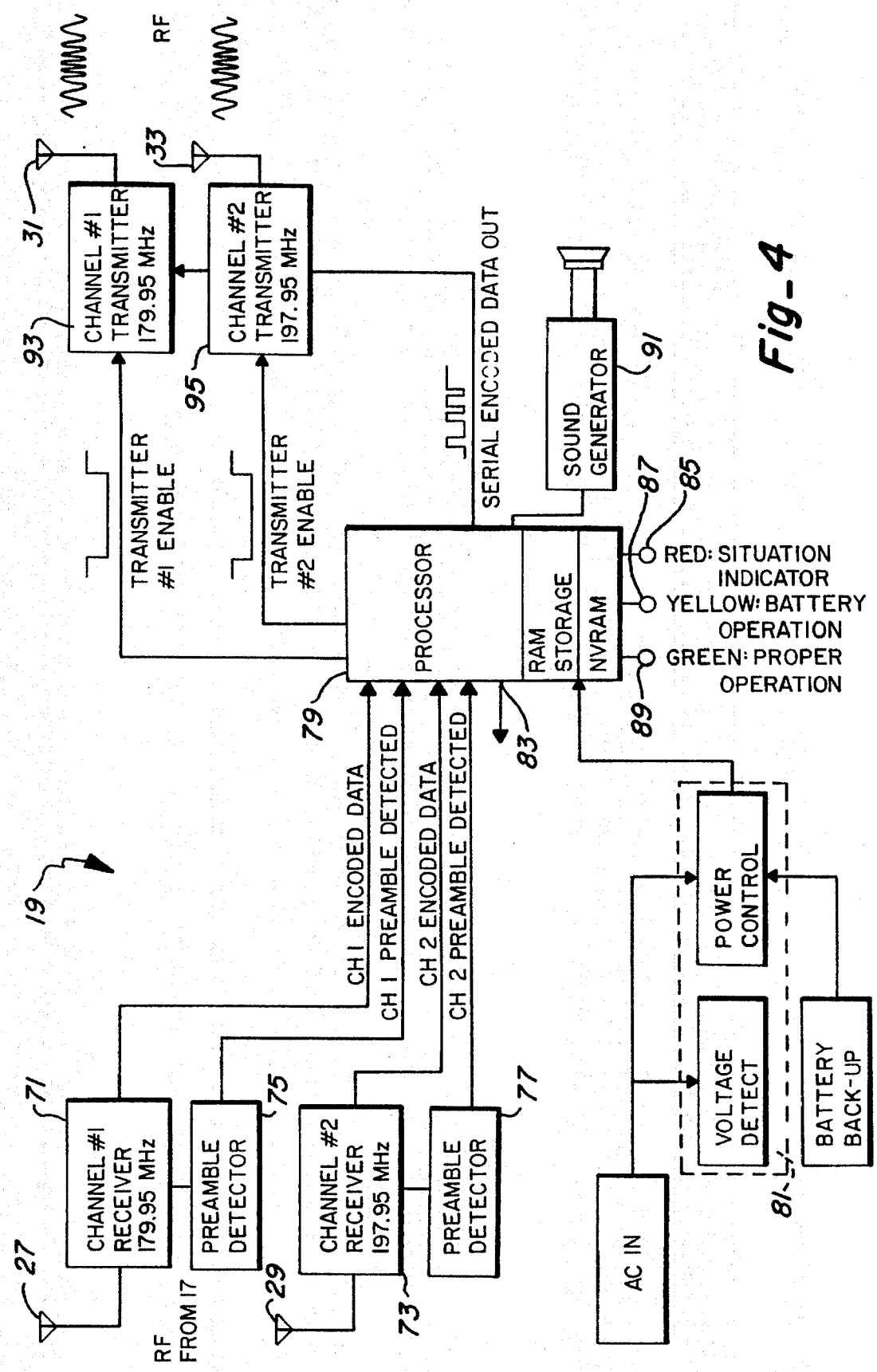
FIG. 4 is a block diagram of the local receiver/secondary transmitter of the apparatus of FIG. 1.

A first embodiment of the overall apparatus 15 of this invention primarily for use as a medical monitor (a plurality of communicating units, various aspects of the invention residing in one or more of the units) is diagrammatically illustrated in FIG. 1. The overall apparatus (or system) includes physiological sensors/processing and transmitting unit 17, local receiver/secondary transmitter unit 19 and remote receiver and alerting unit (for example, a pager) 21. Unit 17 includes dual transmission sources 23 and 25, though as illustrated hereinafter with respect to the preferred embodiment of this invention, a single transmitter could be utilized for use as a personal security monitor. Unit 19 includes dual receiving antennas 27 and 29 and dual transmission sources 31 and 33 and unit 21 includes dual receiving antennas 35 and 37 (again, a single receiver and an auto-dialer, modem or the like, for telephone line transmission could be utilized as discussed hereinafter).

Unit 17, as shown in FIGS. 2, and 3A and 3B, is battery powered, preferably self contained, and is directly mountable on the subject. The unit includes physiological detectors 39 and 41, for sensing and processing respiration and ECG, respectively (other or different physiological detectors could be utilized, for example to detect body temperature, various organ functions, pulse oximetry or the like). Respiration detector 39 includes respiration transducer 43, pressure sensor 45, low pass filter 47 and amplifier 49 and provides an output wave form indicative of each breath of the subject as well as a DC bias signal to maintain baseline.

ECG detector 41 includes electrodes 51, 53 and 55 connected to amplifier 57. The signal from amplifier 57 is filtered at band pass filter 59 (6 to 18 Hz) to provide an output wave form indicative of heart beats of the subject. DC reference generator 61 is provided for generating a bias signal to maintain baseline. The output signals from detectors 39 and 41 are input to processor 63 (for example, a four bit, low power processor) connected with the detectors, where the respiration signal and ECG signal are digitally processed. The output from processor 63 is a serially encoded data stream (a data signal, or word) conveying data indicative of respiration and heart rate (as more fully set forth herein below).

Processor 63 is connected with transmitters 65 and 67 to provide both transmitters with the data signal as well as with independent transmitter enable signals. Low battery detection circuit 69 is connected with processor 63 and provides information indicative of battery status for incorporation into the data signal.

Transmitters 65 and 67 (as schematically illustrated in FIG. 3) are operated at different, non-harmonicly related, frequencies (for example, transmitter 65 at 179.95 MHz and transmitter 67 at 197.95 MHz). The digital data signal is transmitted FSK with direct frequency modulation of the carrier at a total deviation of 6 to 10 KHz (preferably 8 KHz). Transmission range for transmitters 65 and 67, when used in system 15, need only be about 5 meters or less, though greater range could easily be provided.

Figure 5:
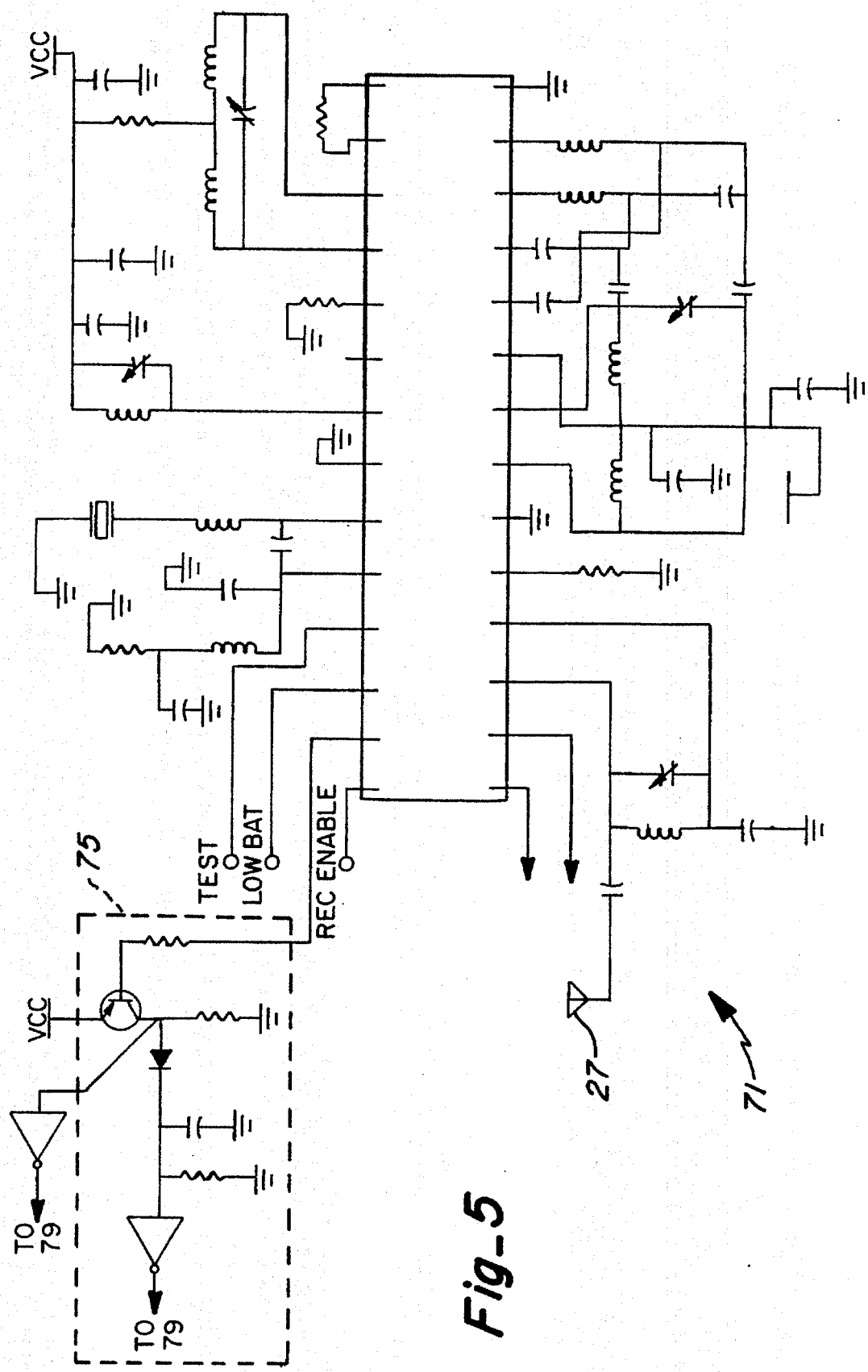
FIG. 5 is a schematic diagram of the receiver and preamble detection circuit of FIG. 4.

Turning to FIGS. 4 and 5, local receiver/secondary transmitter unit 19 includes tuned receivers 71 and 73 (which in most regards are similar and illustrated in FIG. 5 with respect to receiver 71) for receiving different ones of the transmissions from transmitters 65 and 67. Preamble detection circuits 75 and 77 are connected with receivers 71 and 73, respectively, and serve to validate the signals as ones emitted by transmitters 65 and 67 (as more fully set forth hereinafter). The output from circuits 75 and 77 (a signal indicating validity or not of the received transmission) is coupled to processor 79, which is also connected with receivers 71 and 73 to receive the received transmissions (including the encoded data signals).

Unit 19 is preferably an AC powered unit with battery backup (controlled by voltage detecting and power control circuit 81) for occasions of local power failure. Processor 79 includes operational memory (RAM storage) and nonvolatile memory (NVRAM) for storage of data signals as well as time stamping of critical events such as turning on and off of unit 19, AC power interruptions, occurrences of apnea, irregular heart rate activity, irregular breathing patterns, and the like. Such stored information can thus later be retrieved utilizing auxiliary port 83.

Processor 79 is connected with LED readouts 85, 87 and 89 and local sound generator unit 91 providing information, as more fully discussed hereinafter, to a care giver. The output of processor 79 (again the data signals received by unit 19) may be coupled to secondary transmitters 93 and 95 for retransmission to unit 21 when enabled by independent enabling signals received from processor 79. The arrangement and operation of transmitters 93 and 95 is substantially the same as heretofore discussed with respect to transmitters 65 and 67, with the exception that the transmission range of transmitters 93 and 95 is substantially greater (for example, accommodating effective transmissions of about 30 meters or more).

FIGS. 6A through 6C illustrate the data encoding scheme utilized in processors 63 and 79 (FIG. 6A), a sample of a data signal (FIG. 6B), and exemplary transmissions (FIG. 6C) from units 17 and 19. The data signal is a 12 bit data word including a 3 bit valid signal identification, or preamble, a one bit source identification (utilized primarily at unit 21 to indicate whether the transmission is from unit 17, when in range, or unit 19), a 4 bit physiological event count (breaths or heart beats for example) data signal, and a 4 bit status signal (conveying subject status with respect to the monitored physiological event such as apnea, tachycardia, bradycardia, status normality or the like, and system status such as low battery conditions or the like). Data words not preceded by a wake-up signal generated in response to the enable signals from processors 63 or 79 are not received.

Turning now to FIGS. 6C, 7A through 7C, and 8A and 8B, the operation of apparatus 15 will be described with reference to the programming of processors 63 and 79. Processor 63 periodically samples (for example, every one-hundredth of a second) the breath rate analog value (determined in accord with the positive and negative threshold values established and adjusted as shown in FIG. 7A) of the respiration signal received from detector 39. If the value exceeds the positive threshold value, the flag indicating positive threshold crossing (BRPOS) is set and the value is utilized for further evaluation and adjustment, if necessary, of the positive value threshold. If not, and if the value crosses the negative threshold value, and if BRPOS has been previously set, the breath count is incremented by one, transmitter 65 is sent an enabling signal by processor 63, the last established data word is transmitted on transmitter 65, and BRPOS is cleared.

If BRPOS was not previously set, the value is utilized for further evaluation and adjustment, if necessary, of the negative value threshold. If the analog value read does not cross the positive threshold or the negative threshold, the value is utilized to further evaluate the positive and negative value thresholds.

Likewise, processor 63 periodically samples (for example, every one-hundredth of a second) the heart beat analog value (again as established by the positive and negative threshold evaluation scheme shown in FIG. 7B) of the ECG signal received from detector 41. At every sample, a timer is incremented (by one one-hundredth of a second) for purposes of measuring time between a falling (Q) wave and a rising (R) wave (QRTIMER in FIG. 7B). If the value crosses the negative threshold value, a flag (ECNEG) indicating crossing of the negative threshold value is set, QRTIMER is cleared, and the value is utilized for further evaluation and adjustment, if necessary, of the negative value threshold. If not, and if the positive threshold value is not exceeded, the value is utilized only for further evaluation of the positive and negative value thresholds.

If the negative threshold value is not crossed, and the positive value is exceeded, and further if ECNEG has been set and the time counted by incrementing QRTIMER is greater than an established limit (indicating an average time between Q and R threshold), a heart beat is indicated and the beat count is incremented by one. If the apnea flag (discussed hereinafter) has not been set, ECNEG is cleared and the routine ends. If the apnea flag has been set, transmitters 65 and 67 are enabled by a signal from processor 63, the last established data word is transmitted by transmitters 65 and 67, and ECNEG is cleared.

If, in the case where the negative threshold is not crossed and the positive threshold value is exceeded, either ECNEG is not set or the time counted by incrementing QRTIMER is less than the established limit, the value is utilized for further evaluation of the positive value threshold.

Turning now to FIG. 7C, a data word is assemble by processor 63 (for example, every five seconds). The preamble signal, source signal, and physiological event count signal (in this case, the number of breaths taken by the subject in the last 5 seconds as taken from the incremented breath count in FIG. 7A) are assembled. If the battery is low, the battery low bit of the status signal is set. If not, it is cleared.

If the number of breaths since the last data word was assembled equals zero, a timer is incremented by 5 seconds, and if the incremented time is greater than an established threshold (for example, 20 seconds) the apnea flag and bit (of the status signal) are set, transmitters 65 and 67 are each sent an enabling signal, the data signal is transmitted on both transmitters (as discussed heretofore with respect to FIG. 7B, as long as the apnea flag is set each heartbeat detected will generate a signal on transmitters 65 and 67, an updated data signal also being transmitted every five seconds on both transmitters), and incremented heart beat count and breath count are set at zero.

If the incremented time is less than the established threshold, or if the number of breaths since the last data word was assembled is greater than zero (whereupon the incremented time is set at zero), if the number of heart beats either exceed a preset average heart rate range or drop below the range the appropriate bit of the status signal is set. If heart rate is within the normal range, a status normal bit of the status signal is set. Transmitter 67 is then sent an enabling signal from processor 63, a transmission is emitted, and incremented heart beat count and breath count are set at zero.

As illustrated in FIG. 8A and 8B, processor 79 of local receiver/secondary transmitter unit 19 continually samples for detected RF transmissions at receivers 71 and 73. If an RF signal is detected at receiver 71, and if the preamble was validated by preamble detection circuit 75 the remaining bits (after the preamble) of the data word are read, the transmission is decoded (and the data word is reassembled), and a signal from processor 79 enables transmitter 93 for retransmission of the data signal to remote receiver unit 21.

If apnea is indicated (by a status bit), LED 85 is lit and, for medical applications, sound generator 91 sounds an alarm. If either tachycardia or bradycardia is indicated by a status bit, LED 85 is caused to blink and sound generator 91 sounds an alarm. If a status bit indicates a low battery at unit 17, LED 87 is caused to blink. If the local transmitter battery is in use and is low, LED 89 is caused to blink. If a breath is detected (as would normally be the case when a transmission is received by receiver 93) sound generator 91 issues a click. Thereafter, the received data word is stored in memory.

After date storage, or where either no RF signal is detected or a non-validated transmission is detected, receiver 73 is checked for receipt of an RF signal. If no RF signal is detected, or if a non-validated transmission is detected, processor 79 returns to sample receiver 71 for detection of an RF signal. If a validated preamble is detected by preamble detection circuit 77, the remaining bits of the received data word are read, the transmission is decoded (and the data word is reassembled), and a signal from processor 79 enables transmitter 95 for retransmission of the data signal to remote receiver unit 21.

Thereafter the data word is analyzed, responded to and stored as heretofore discussed with respect to transmissions received by receiver 93, and processor 79 again samples for detection of an RF signal on receiver 71.

As may be appreciated from the foregoing, apparatus and methods are provided for the remote monitoring of selected physiological parameters for medical monitoring purposes. Many of the concepts utilized thereby will be readily seen to be applicable to the security monitoring system hereinafter described.

FIGS. 9, 10 and 11 illustrate the preferred embodiment of this invention for use as a personal security monitor. Breath detector 100 and monitor/radio transmitter module 101 (shown in FIG. 9 in a belt configuration (as discussed hereinafter), it being understood that other configurations are possible) are carried on the person being monitored. Base station 103 includes radio receiver 105, automatic telephone dialer 107 (any of the known types of auto-dialers, modems or the like could be utilized), and base station controls and indicators 109 all connected with processor 111. Located at distance from the user, monitoring station 113 monitors calls initiated by the user-side base station and initiates helpful action.

Radio transmitter module 101 is worn or carried by the person using the system. Base station module 103 listens for a transmission from module 101, which carries an identity code, as heretofore discussed, and activates automatic telephone dialer 107 when a transmission from the user module is received (which transmission occurs only when the user so intends as hereinafter set forth). Base station 103 sends the identity of the user to the remote monitoring station and has the capability of seizing the line if the telephone is in use or off-hook for any reason.

As shown in FIG. 10, module 101 includes breath detector 115, the output of which is coupled to processor 117. Unit power is 'supplied by battery module 119. Selector bank (for example a DIP switch bank) 121 is connected to processor 117 and allows user selection of a predetermined breathing pattern from a plurality of possible selections, recognition of which by processor 117 will cause an alarm output.

The output from processor 117 is a signal including a preamble, as heretofore discussed to identify the signal, and a coded indication of an alarm condition. The output triggers vibrator driver 123 connected to vibrator 125 to provide an indication to the user that an alarm will thereafter be sent within a preset (in software) time period. This both informs the user that the predetermined breathing pattern has been properly executed, where a circumstance so merits, and allows the user to cancel the sending of the alarm (by closing switch 127) during the preset time period thus avoiding false alarms.

Instant transmission request switch 129 allows the user to manually initiate an alarm signal. The alarm signal is sent by way of radio frequency transmitter 130 and antenna 131 to base station 103.

While any number of known breath detectors could be utilized with this invention, FIGS. 12A through 22 illustrate the preferred embodiments of breath detector 100 and means for attaching monitor module 101 and detector 100 to the user's body.

FIGS. 12A and 12B illustrate monitor 101, including breath detector 100. In this embodiment, breath detector 100. Associated circuitry 101 may be independently housed for attachment to the subject (for example, by clipping on a belt or wearing in a pocket) or may be incorporated with detector 100 into a single, belt like structural unit as illustrated in FIGS. 9, 17 or 21.

Detector 100 is formed from a length of flexible yet resilient tubing (any length, depending on desired responsiveness desired by the particular application, may be employed from a length sufficient to wrap entirely around the subject as shown in FIG. 12A to very short lengths as shown in FIGS. 21 and 22), such as 602-305 Silastic (a trademark of Dow Corning Corporation) medical grade tubing, which, due to the relationship of material durometer, wall thickness and/or tube diameter, automatically regains its shape (both in terms of length and cross-sectional shape) after subjection to any mechanical deforming force such as stretching, flattening, kinking or the like.

In one embodiment, the tubing has a circular cross section (though an elliptical or other curvilinear cross section would also be effective), with a 0.078" inside diameter and a 0.125" outside diameter. The tubing is preferably made of silicon or similar material having a durometer of about Shore A54 and a wall 132 (FIG. 13) thickness of about 0.047", though any wall thickness and material could be utilized which exhibits the desired characteristics. It should be understood that the material utilized must not be so stiff or rigid that it will not yield to forces tending to change its geometry, nor so soft or flexible that the tube will not regain its shape after deformation and/or be easily kinked. Wall thickness will be related to external noise entering into the system.

The simplified structure of detector 100 presents a clear advantage over prior art devices which require substantial additional structure, such as a foam rubber insert, to assure that the fluid cavity will regain its undeformed geometry (see U.S. Pat. Nos. 4,602,643 and 4,813,428). Furthermore, the small diameter tubing greatly reduces pressure, or air movement, exerted at the pressure sensor (as hereinafter set forth) thus overcoming the need for specialized housings, barrier structures, secondary pressure chambers and the like which might be necessary where greater pressure and/or volumes of air are being exerted at the sensor. The foregoing greatly simplifies manufacture and reduces the likelihood of component failure while providing a reliable output indicative of subject respiration, and, in some embodiments, a more readily differentiatable output from the monitor.

Tube 100 can be of any length (see, for example, FIGS. 9 and 21), but in its simplest form, as shown in FIG. 12A, is of a length sufficient to circle the entire torso of the subject (either inside or outside of the subject's clothing). The tube is configured so that but a single outlet 133 from channel, or conduit, 134 is provided. This may be accomplished utilizing tee junction 135 (as shown in FIGS. 12A and 14) having three access openings, plugs 136 in end or ends 137 (as shown in FIGS. 16, 17 and 18), or in any other manner consistent with the goal of creating a fixed internal volume of the tube or tubes having a single outlet.

Small diameter flexible tube 100 thus contains a fixed volume of fluid (preferably air), with the volume of channel 134 of tube 100 being altered by the breathing of the subject thereby causing low frequency pressure variations at outlet (or outlets) 133. Using, for example, Silastic tubing from Dow Corning Corporation, when the flexible tubing is placed snugly on the subject it will stretch (lengthen) during inhaling. While this stretching tends also to diminish tube diameter (at least along some of its length), since the tube length increases more than the diameter decreases, overall tube volume increases thus lowering fluid pressure in the tube. When exhaling occurs, the resiliency of the material causes the tube to return to its original shape (or, in the case of more complete evacuation of the lungs, to a shape approaching its shape when not snugly secured around the subject), thereby decreasing tube volume and increasing fluid pressure in the tube.

In the embodiment of the invention illustrated in FIGS. 12 and 13, interconnecting tube 138 (of any length suitable for its intended reach) is utilized to connect detector 100, at outlet 133, to pressure transducer manifold 139 connected (for example by a sealing adhesive) with transducer housing 140 having pressure transducer 141 of circuitry 101 therein.

Transducer 141 can be any type of pressure transducer. However, an electret capacitor microphone has been found to be preferable, providing a signal with good signal to noise ratio at its output 141 or 143. Electret microphone transducer 141 is mounted in housing 140 without need of any isolating film or the like utilized in other devices (see U.S. Pat. No. 4,813,428) to prevent over pressurization at the location of transducer 141 and/or saturation of the output. This is so because, unlike prior art devices utilizing larger pneumatic sensing cavities, tube 100 creates only relatively small changes in pressure at outlet 133 responsive to respiration or other movement.

The output signal from transducer 141, indicative of a subject's breathing patterns, is input to active low pass filter 145 having a center frequency of about 2 Hz and approximately 24 DB/octave attenuation. Filter circuit 145 (as more fully described with reference to FIG. 4) reduces artifact in the signal due to subject movement and/or non-breathing related impacts on detector 100. The output signal from filter 145 is provided at processor 117, the output of which is used to modulate transmitter 130 (operating at any selected frequency and being either AM or FM modulated) for application at antenna 131 for broadcast to base station 103.

Turning now to FIG. 15, low pass filter 145 is illustrated. Filter 145 has a cut-off frequency of between about 0.5 and 3 Hz (the lower end providing the best result in terms of movement artifact reduction in the signal but also reducing the upper limit of the detected respiration frequency), and preferably a cut-off at about 2.2 Hz. The embodiment of filter 145 illustrated is an active, four pole low pass configuration (known as an infinite gain, multiple feedback low pass filter with a Butterworth response). This configuration minimizes the frequency response changes due to component tolerance.

Resistor 161 and diode 159 are used to bias amplifiers 155 and 157 (for example, Linear Technology LT1179 operational amplifiers). Since this infinite gain, multiple feedback configuration is an inverting one, amplifiers 55 and 57 together provide an output that is in phase with the input from the subject (i.e., a positive going signal is output responsive to the subject's inhaling). Transducer 141 (herein a Digi-Key P9932 or equivalent) provides an increased current at its output responsive to increased fluid pressure at its input. Utilizing the material above described for tube/detector 100, wherein the volume of the tube increases due to tube deformation caused by inhaling, when the subject inhales a decreased fluid pressure results in the tube, thereby providing a negative going output voltage. Since this signal in inverted by filter circuit 145, a positive output voltage is output from filter circuit 145, thus being in phase with the input, a breath taken by the subject. Upon exhaling, the reverse is true (i.e., a negative output voltage from filter circuit 145 occurs).

Figure 19:
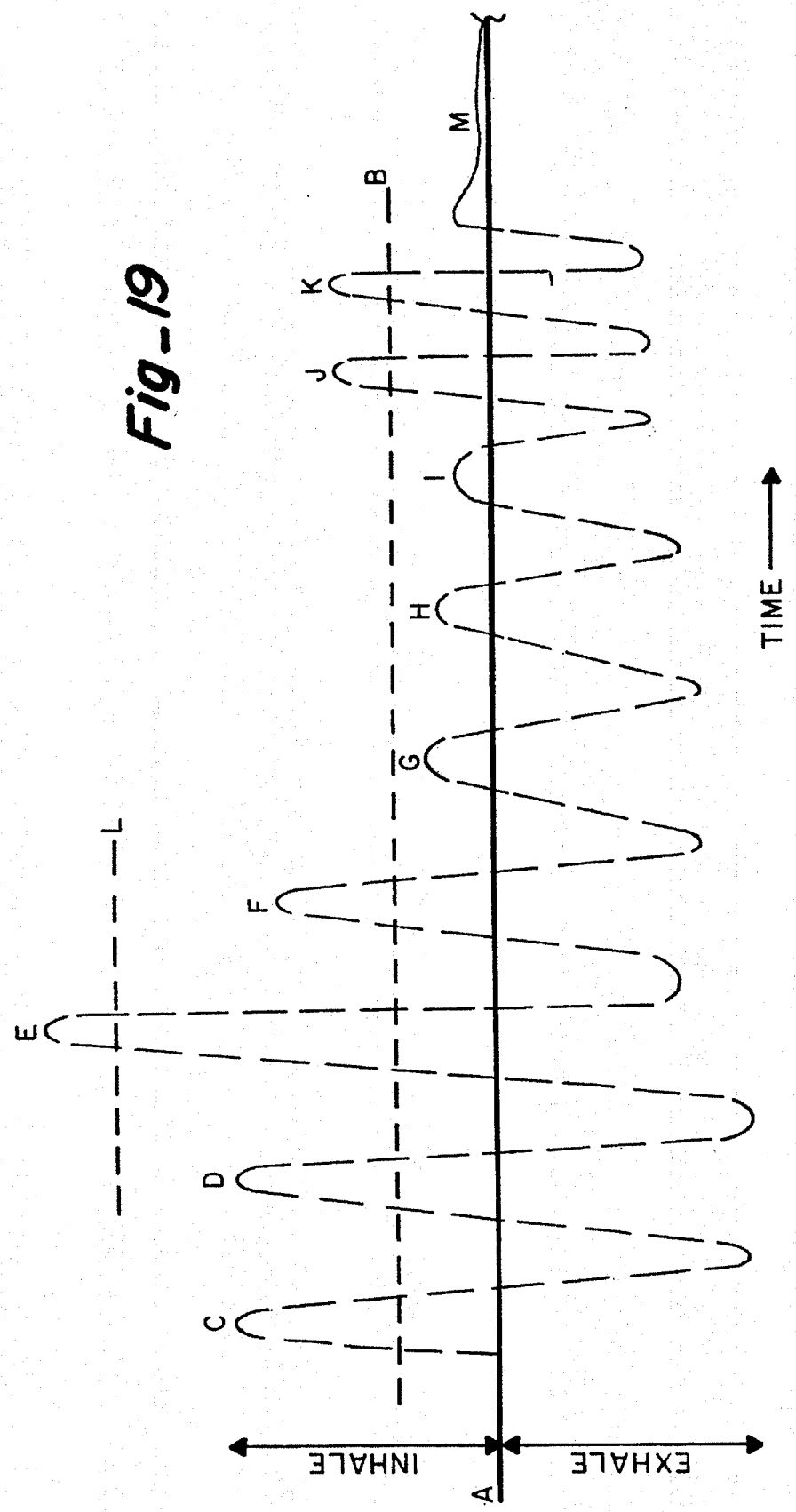
FIG. 19 is an illustration of exemplary waveforms output from the respiration detector of this invention.

FIG. 19 illustrates the output signal waveform from filter 145 with line A indicating the reference level below which exhaling is indicated and above which inhaling is indicated. The level indicated by line B is established (by appropriate processing) as a breath detection threshold. Signals, including noise, which do not achieve threshold B are interpreted as no breath. Thus, pulses C, D, F, J and K indicate normal breathing, though of different rates. Pulse E exceeds a second threshold L (again established in software, where desired) which indicates a sigh or yawn.

Obstructive apnea is indicated by pulses G, H and I because threshold B is not reached and the amplitude below reference level A exceeds the amplitude of the waveform above level A (of course the reverse situation could also be true, software being configured to accommodate either occurrence). Waveforms J and K, by virtue of slightly decreased amplitude but increased frequency, indicate more rapid, shallower breathing. As the waveform at M approaches level A, a cessation of breathing is indicated.

The amplitude of the signal above reference A will be proportional to the volume of air drawn into the lungs and the amplitude of the signal below reference A will be proportional to the volume of air and $CO_2$ expelled from the lungs. As may be appreciated, utilizing the above described system, those monitoring the subject's breathing are better able to distinguish various breathing patterns and events (such as obstructive apnea, breath holding, yawning and the like) from one another.

Means of securing detector 100 around a subject is illustrated in FIG. 16. In this arrangement, one end 137 of tube 100 is plugged utilizing any suitable, preferably flexible, material 136, and tee 165 is modified by plugging access 167. A Velcro (or similar material) loop pad 169 of a selected length is provided for variably positionable receipt of Velcro hook pads 171 and 173. Pad 171 has end 137 of detector 100 secured thereto at each side of plug 136 (for example, using stainless steel staples), and pad 173 has tee 165 affixed thereto (for example, by stitching or the like). In this manner, the detector can be positioned around the subject sufficiently snugly to achieve volume deformation during breathing, and can accommodate subjects of differing girth.

FIG. 17 shows a preferred arrangement of the monitor, all of which, including detector 100, transducer 141, filter 145, processor 117, transmitter 130 and antenna 131, are incorporated into a wearable unit. As previously shown in FIG. 16, a Velcro loop pad 169 and hook pad 171 are provided. However, transducer 141, filter 145, processor 117, transmitter 130 and antenna 131 are mounted modularly to pad 169 (for example using a fabric substrate and a conformal coating or the like, with a protective cover) using an adhesive or other suitable means for attachment. Manifold 139 is then utilized to receive directly end 175 (outlet 133 from channel 134) of detector/tube 100, thus providing a compact wearable monitor.

An alternative embodiment of the breath detector of this invention, utilizable with any of the arrangements illustrated in FIGS. 12, 16 or 17, is shown in FIG. 18. Multiple tubes 100 are arranged for application around the subject, the tubes each having a single outlet joined at manifold 177 to again provide a single known volume or capacity. Use of multiple tubes will increase detector sensitivity and improve artifact rejection of the overall system.

Figure 20:
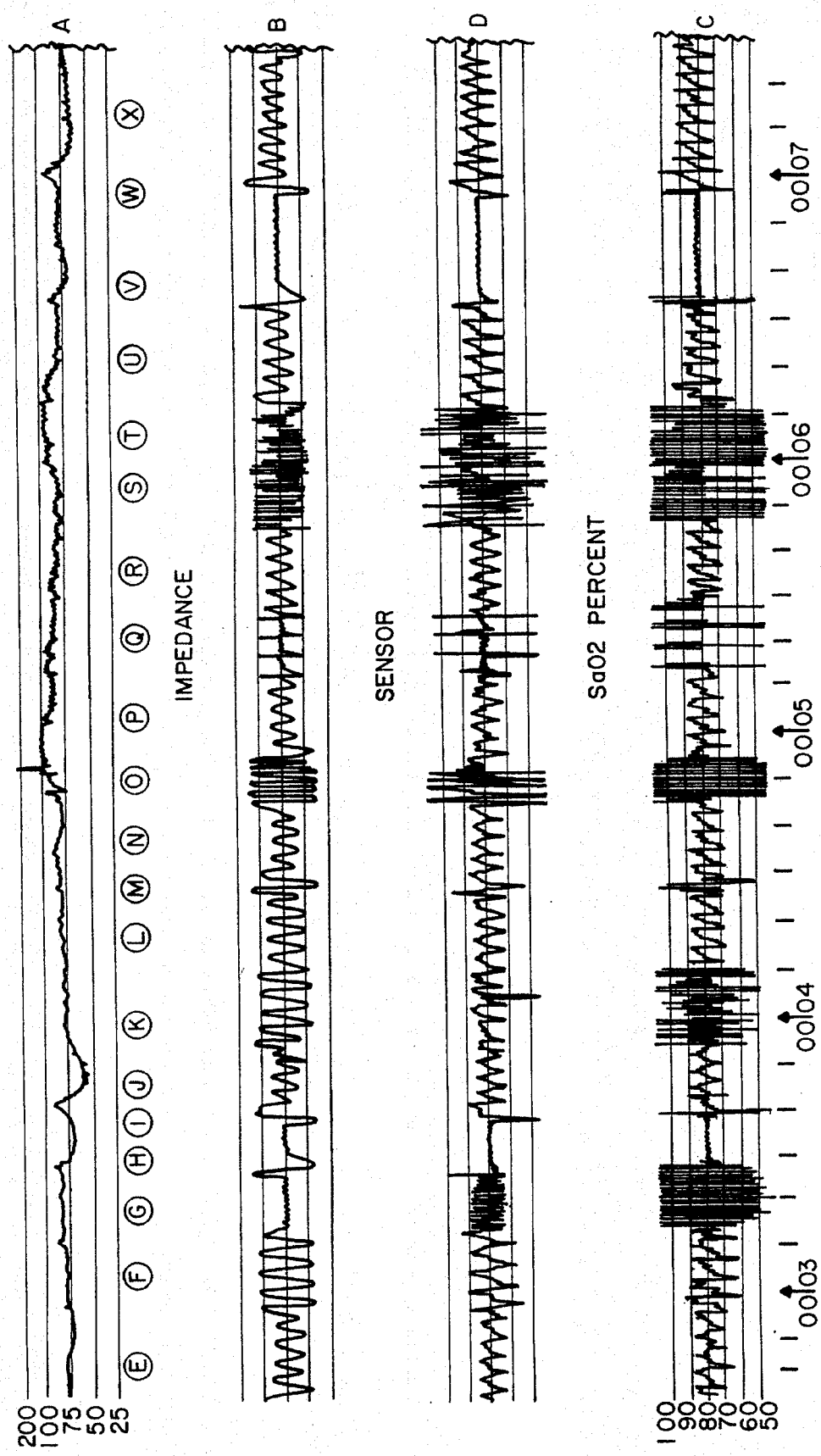
FIG. 20 is a chart illustrating actual waveforms of the monitor of this invention (both filtered and unfiltered) compared with the output of a prior art pneumographic monitor.

FIG. 20 shows data comparing waveforms for average heart rate of a subject (A), a prior art impedance pneumographic monitor (B), the unfiltered output from transducer circuitry of the monitor of this invention (C), and the filtered output from monitor 101 of this invention (D). Regular breathing is shown at E, J, L, N, P, R, U and X, and deep breathing is shown at F. Holding of breath (cessation of breathing) is shown at H and V. Of particular note, however, is the ability of monitor 101 to more clearly distinguish fast shallow breathing (G) from cessation of breathing (H and V). Also note that the output of monitor 101 goes positive and then level at H and V while the prior art monitor goes positive and then negative before the held breath (of key importance in differentiating obstructive apnea). I and W indicate release of the held breath.

The application of monitor 101 to distinguish and monitor obstructive apnea is further illustrated at Q (slow obstructive apnea) and S (fast obstructive apnea). Because the output waveform is in phase with the actual respiratory event, unlike the prior art unit, three distinct episodes of chest cavity fluctuation (the waveform first goes in a negative direction, then in a positive direction) are detected (unlike the prior art device which first goes positive with the negative transition, quite similar to holding ones breath). By counting the pulses, the monitor can determine the number of times the chest cavity has fluctuated during obstructive apnea.

At K, normal breathing while shaking tube 138 is illustrated. The movement artifact is quite pronounced in the unfiltered output (C) of monitor 101, while the filtered output (D) clearly shows the effectiveness of filter 145 in removing signal not indicative of breathing (the filtered output indicating normal breathing).

At M, the occurrence of a sigh is more clearly registered by monitor 101. At O and T (occurrences of coughing and crying, respectively), while both signals B and D indicate that something unusual is occurring, because of the use of electret transducer microphone 141 in the configuration of monitor 101 as set forth herein, the signal from monitor 101 may be linked to an amplifier and speaker (or earphones) and the actual sound of coughing or crying of the subject will be heard (which is not the case with the prior art device).

FIG. 21 illustrates another particularly useful embodiment of the detector with this invention wherein tube 100 is substantially shortened (as before, however, function is the same). Loop pads 169 are attached (for example, by sewing) at opposite ends of belt 180 for receipt of the detector/monitor system snugly adjacent to the subject's torso when belt 180 is applied therearound.

Yet another useful embodiment 182 of this invention is illustrated in FIG. 22. Herein, rather than tube 100 being utilized, a flexible yet resilient bulb 184 connected to manifold 139 is utilized to detect breathing. As bulb 184 (akin to an eye dropper bulb) is flexed due to inhaling and returns to its initial shape during exhaling, fluid pressure changes within the bulb are sensed at transducer 141. It should be noted, however, that during inhaling, the volume of bulb 184 is reduced due to bulb deformation, while volume is increased during exhaling when bulb 184 returns to its original shape. Thus, an increase in output voltage from transducer 141 is indicative of inhaling (increased fluid pressure results at transducer 141 due to decreased volume). A variety of alternative designs, such as bellows type structures, could be utilized for the breath detector of embodiment 182.

FIG. 23 illustrates a transmitter 130 which may be used with this personal security monitor, though other known transmitter (including dual transmitters as set forth hereinabove) may be used.

FIG. 24 shows the processor arrangement used in this invention (for example, a Toshiba TMP 47C860F 4 bit low power microprocessor operable between 2.7 and 5 volts power supply with a 455 Khz operating frequency and internal A to D conversion).

The personal security monitoring system of this invention is programmed to alarm automatically upon its recognition of an emergency condition as represented by deviations from normal physiological patterns, such as voluntary alteration of normal breathing patterns by the user corresponding to that input at selector bank 121.

The breath wave form shown in FIG. 25 received from breath detector 115 consists of the inhale portion C and the exhale portion D about a reference A. The peak inhale E is the maximum excursion as an individual inhales. The peak exhale F is the maximum excursion as a person exhales. A legitimate breath is detected if breath exceeds the high threshold crossing B and exceeds the low threshold crossing G. These thresholds are variable, and move up and down through automatic gain control (in software) the peaks move. The peaks E and F change (i.e., move up and down) and thus the thresholds need to be recalculated.

Every peak which occurs that is higher than the threshold H are averaged into a pool of samples of peaks and threshold B is then some set percentage (for example, 7%) less than the value of the average of this peak pool. The same thing occurs for lower threshold G. All the negative peaks below threshold I are pooled together and the lower threshold G is then some set percentage greater than the average for these negative peaks. The high and low thresholds B and G can move to a value that the hardware will allow down to a minimum that is 7% above the reference threshold, and thresholds B and G cannot move lower or higher, respectively, than this value. A valid breath is detected by the positive crossing of the high threshold B followed immediately by a negative crossing of the low threshold G in that order.

Breath information (i.e., raw analog data) is provided from detecting circuit 115 to processor 117 where internal analog to digital converter converts the data. The software then determines whether a breath occurs and establishes and updates the user's normal breathing patterns. The software also determines when a sequence of breaths or lack of breaths matching the preselected input is present thus indicating whether an alarm should be transmitted.

The software is programmed to establish three software partitions. As shown in FIG. 26, breath detect section (partition 1) reports the occurrences of an actual breath to partition 2, called the breath pattern analyzer, and controls additions to the various peak pools.

The breath pattern analyzer utilizes the data from partition 1 and the inputs selected by the user at switch bank 121 to distinguish between normal patterns and a preselected pattern of breathing utilized to indicate and emergency.

Figure 27:
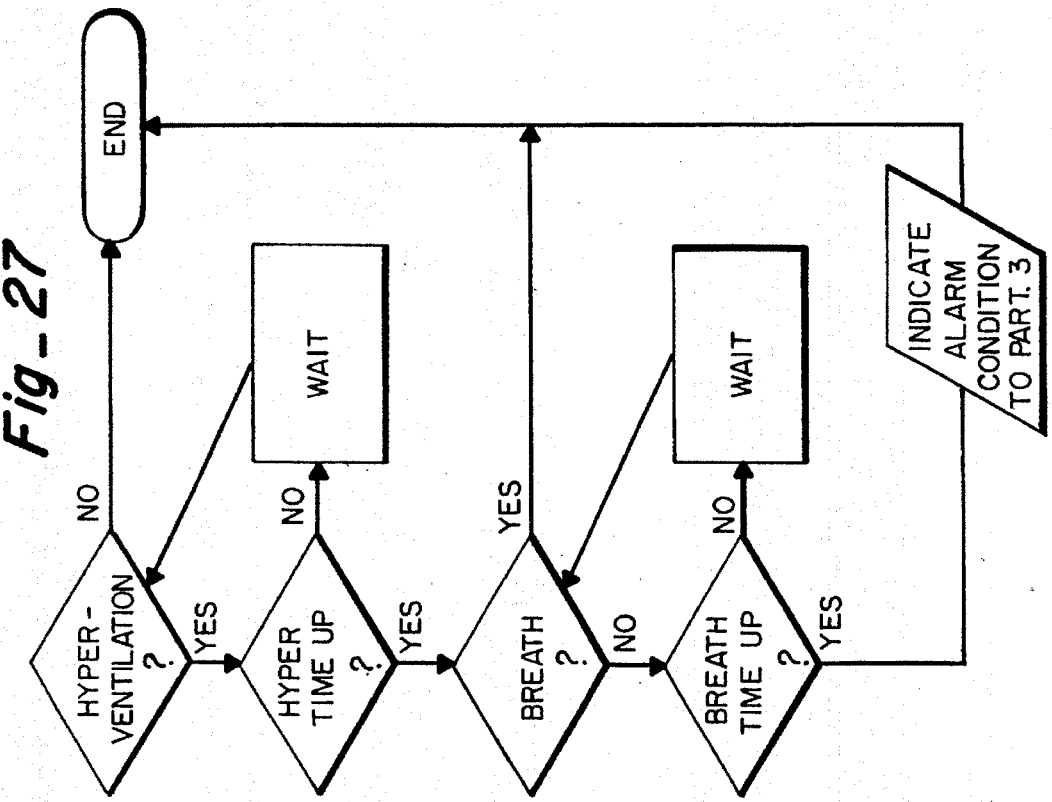

For example, if switches C and D are closed, the analyzer would be looking for a fast breathing pattern from partition 1 (randomly defined, for example, a 2 or more breaths per second) which must occur for five seconds followed by holding ones breath for an additional five seconds. These two conditions would cause an alarm output to partition 3 (see FIG. 27).

Figure 28:
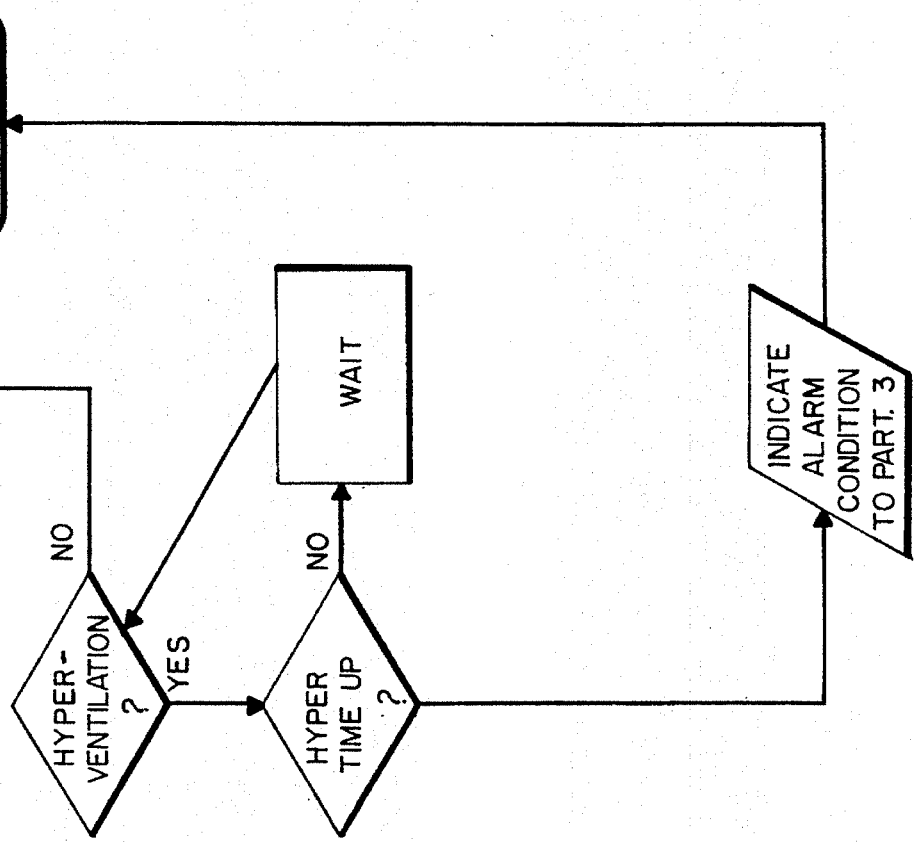

If switches A and E, F or D are closed, a fast breath rate for the requisite number of seconds would indicate alarm (see FIG. 28).

Figure 29:
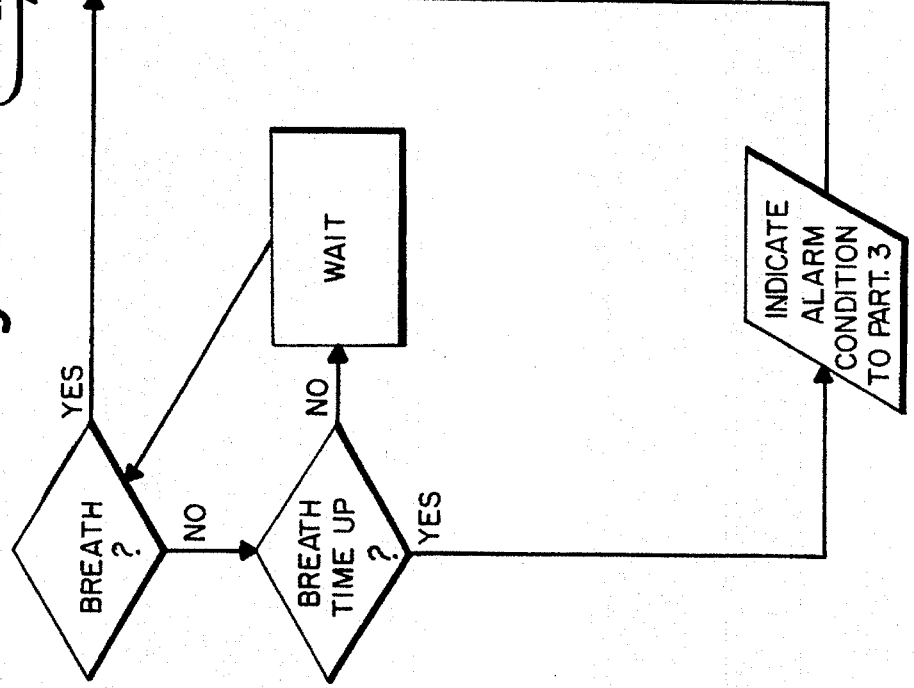

If switches B and E, F or D are closed, cessation of breath for a total of the programmed seconds would indicate alarm (see, FIG. 29).

Figure 30:
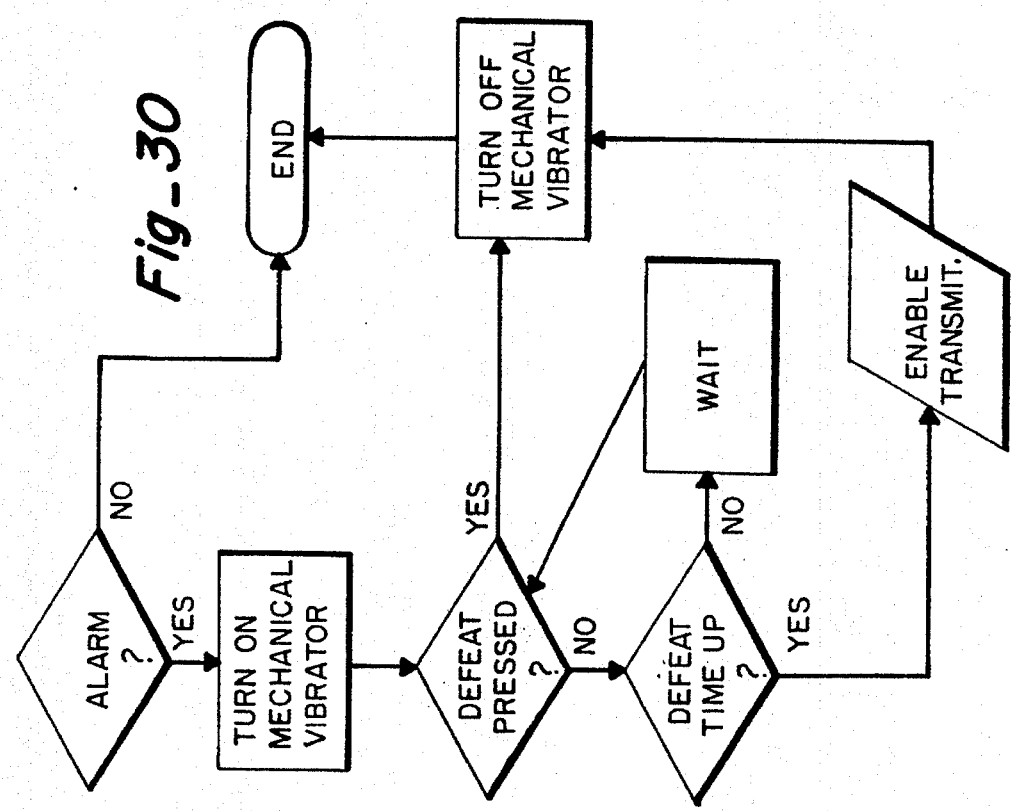

As shown in FIG. 30, software partition 3 controls activation of the user indicator and transmitter enablement (after the preset delay period).

The time for an individual to hold his/her breath or to breath extra fast can be either continuously variable, pre-set in software or switch selectable as shown.

As may be appreciated, improved personal security monitoring is provided which allows for discreet, hands free initiation of a silent alarm.

What is claimed is:

1. For use in a personal security monitoring system, a compact body mountable monitor comprising:

a breath detector providing an output indicative of a user's respiration;

means for receiving said output from said breath detector and utilizing said received output to distinguish between the user's normal breathing pattern and a preselected other breathing pattern to be intentionally executed by the user when in distress; and output means connected with said means for receiving said output for providing an alarm signal only upon recognition of said other breathing pattern.

2. The monitor of claim 1 further comprising a selector connected with said means for receiving said output for user selection of said other breathing pattern from a plurality of possible other breathing patterns.

3. The monitor of claim 2 wherein said selector includes means for respiration pace selection, including at least a rapid breathing selection, and means for period selection to select the time over which said pace selection will occur in order to be recognized as said preselected other breathing pattern.

4. The monitor of claim 1 wherein said output means is a radio frequency transmitter.

5. The monitor of claim 1 further comprising an indicator connected with said means for receiving said output and providing an indication to the user that said other breathing pattern has been recognized, and wherein said means for receiving said output delays an indication of said recognition to said output means for a selected period after said indication to the user.

6. The monitor of claim 5 further comprising alarm signal cancelation means connected with said means for receiving said output for user cancelation of said alarm signal during said selected period.

7. A personal security monitoring system comprising:

a monitor associated with a user to be monitored and including a breath detector providing an output indicative of a user's respiration;

a selector for user selection of a selected breathing pattern from a plurality of possible breathing patterns, said selector including means for respiration pace selection, including at least a rapid breathing selection and a breathing cessation selection, and means for period selection to select the time over which said pace selection will occur in order to be recognized as said selected breathing pattern; and a processor receiving said output from said breath detector and said user selection of a selected breathing pattern from said selector, said processor utilizing said received output to distinguish between the user's normal breathing pattern and said selected breathing pattern and providing an alarm output only upon recognition of said selected breathing pattern.

8. The system of claim 7 wherein said monitor includes a transmitter for transmitting a signal indicative of said alarm output.

9. The system of claim 7 further comprising means for receiving said transmitted signal from said transmitter and retransmitting said alarm output to a monitoring station.

10. The system of claim 9 wherein said means for receiving and retransmitting includes an automatic telephone dialer.

11. The system of claim 7 further comprising an indicator connected with said processor and providing a substantially inaudible indication to the user that said selected breathing pattern has been recognized.

12. The system of claim 7 further comprising means for discretely mounting said monitor on the user's body.

13. A method for monitoring personal security comprising:

detecting respiration of a person to be monitored;

utilizing said detected respiration to establish the person's normal breathing patterns;

selecting another breathing pattern to be intentionally executed by the person when in distress;

distinguishing between said established normal breathing patterns and said another breathing pattern when executed by the person; and providing an alarm signal upon recognition of said another breathing pattern.

14. The method of claim 13 further comprising constantly updating said normal breathing patterns.

15. The method of claim 13 wherein the step of selecting another breathing pattern includes selection of any of a plurality of predetermined possible other breathing patterns.

16. The method of claim 13 wherein the step of selecting another breathing pattern includes selection of a breathing pace and selection of a period over which said breathing pace will occur in order to be recognized as said another breathing pattern.

17. The method of claim 13 wherein said alarm signal is a radio frequency transmission, said method further comprising receiving said transmission remotely from the person.

18. The method of claim 13 further comprising inaudibly indicating recognition of said another breathing pattern to the person.

19. The method of claim 18 wherein said inaudible indication to the person precedes by a selected time period said alarm signal, said method further comprising enabling cancelation of said alarm signal by the person during said time period.

* * * * *